United States Patent
Longhini et al.

(10) Patent No.: US 8,195,296 B2
(45) Date of Patent: Jun. 5, 2012

(54) APPARATUS FOR TREATING STRESS AND URGE INCONTINENCE

(75) Inventors: Ross A. Longhini, Stillwater, MN (US); Yosef Gross, Mashav Mazor (IL)

(73) Assignee: AMS Research Corporation, Minnetonka, MN (US)

(*) Notice: Subject to any disclaimer, the term of this patent is extended or adjusted under 35 U.S.C. 154(b) by 1243 days.

(21) Appl. No.: 11/418,790

(22) Filed: May 5, 2006

(65) Prior Publication Data

US 2007/0260288 A1 Nov. 8, 2007

Related U.S. Application Data

(60) Provisional application No. 60/779,219, filed on Mar. 3, 2006.

(51) Int. Cl.
*A61N 1/18* (2006.01)

(52) U.S. Cl. ............ 607/41; 607/40; 607/143

(58) Field of Classification Search ........... 607/39–41
See application file for complete search history.

(56) References Cited

U.S. PATENT DOCUMENTS

| | | | |
|---|---|---|---|
| 3,628,538 A | 12/1971 | Vincent | |
| 3,640,284 A | 2/1972 | De Langis | |
| 3,646,940 A | 3/1972 | Timm | |
| 3,650,276 A | 3/1972 | Burghele | |
| 3,662,758 A | 5/1972 | Glover | 128/419 |
| 3,667,477 A | 6/1972 | Susset | |
| 3,866,613 A | 2/1975 | Kenny | |
| 3,870,051 A | 3/1975 | Brindley | |
| 3,926,178 A | 12/1975 | Feldzamen | |
| 3,941,136 A | 3/1976 | Bucalo | |
| 3,983,865 A | 10/1976 | Shepard | |
| 3,983,881 A | 10/1976 | Wickham | |
| 4,010,758 A | 3/1977 | Rockland et al. | |
| 4,023,574 A | 5/1977 | Nemec | |
| 4,044,774 A | 8/1977 | Corbin et al. | |
| 4,106,511 A | 8/1978 | Erlandsson | 128/407 |
| 4,136,684 A | 1/1979 | Scattergood | |

(Continued)

FOREIGN PATENT DOCUMENTS

DE 8506522.6 U1 6/1985

(Continued)

OTHER PUBLICATIONS

European Search Report and Written Opinion of 06011641.5 completed Aug. 21, 2006.

(Continued)

*Primary Examiner* — Carl H Layno
*Assistant Examiner* — Natasha N Patel
(74) *Attorney, Agent, or Firm* — Kimberly K. Baxter; Gregory L. Koeller

(57) ABSTRACT

Apparatus is provided, including an implantable mechanical support, shaped to support a portion of a urethra of a patient. One or more electrodes are coupled to the mechanical support, so as to contact tissue of the patient when the mechanical support is implanted in the patient. A control unit drives the electrodes to apply a current to the tissue. A method for treating a patient is also provided, including implanting a mechanical support in a position that supports a urethra of a patient. In response to increased pelvic pressure of the patient, a substance stored in a portion of the mechanical support that is not under the urethra is moved to a portion of the mechanical support that is under the urethra. Other embodiments are also described.

45 Claims, 12 Drawing Sheets

U.S. PATENT DOCUMENTS

| | | | |
|---|---|---|---|
| 4,139,006 A | 2/1979 | Corey |
| 4,153,059 A | 5/1979 | Fravel |
| 4,157,087 A | 6/1979 | Miller |
| 4,165,750 A | 8/1979 | Aleev |
| 4,177,819 A | 12/1979 | Kofsky |
| 4,222,377 A | 9/1980 | Burton |
| 4,290,420 A | 9/1981 | Manetta |
| 4,387,719 A | 6/1983 | Plevnik |
| 4,402,328 A | 9/1983 | Doring |
| 4,406,288 A | 9/1983 | Horwinski |
| 4,414,986 A | 11/1983 | Dickhudt et al. |
| 4,431,001 A | 2/1984 | Hakansson |
| 4,457,299 A | 7/1984 | Cornwell |
| 4,492,233 A | 1/1985 | Petrofsky |
| 4,515,167 A | 5/1985 | Hochman |
| 4,542,753 A | 9/1985 | Brenman |
| 4,568,339 A | 2/1986 | Steer |
| 4,569,351 A | 2/1986 | Tang |
| 4,571,749 A | 2/1986 | Fischell |
| 4,580,578 A | 4/1986 | Barsom |
| 4,585,005 A | 4/1986 | Lue et al. |
| 4,602,624 A | 7/1986 | Naples |
| 4,607,639 A | 8/1986 | Tanagho |
| 4,628,942 A | 12/1986 | Sweeney |
| 4,688,575 A | 8/1987 | DuVall |
| 4,703,755 A | 11/1987 | Tanagho |
| 4,731,083 A | 3/1988 | Fischell |
| 4,739,764 A | 4/1988 | Lue |
| 4,750,494 A | 6/1988 | King |
| 4,771,779 A | 9/1988 | Tanagho |
| 4,785,828 A | 11/1988 | Maurer |
| 4,881,526 A | 11/1989 | Johnson |
| 4,913,164 A | 4/1990 | Greene et al. |
| 4,941,874 A | 7/1990 | Sandow et al. |
| 5,013,292 A | 5/1991 | Lemay |
| 5,019,032 A | 5/1991 | Robertson |
| 5,082,006 A | 1/1992 | Jonasson |
| 5,094,242 A | 3/1992 | Gleason |
| 5,103,835 A | 4/1992 | Yamada et al. | 128/734 |
| 5,112,344 A | 5/1992 | Petros et al. |
| 5,193,539 A | 3/1993 | Schulman |
| 5,193,540 A | 3/1993 | Schulman |
| 5,199,430 A | 4/1993 | Fang |
| 5,285,781 A | 2/1994 | Brodard |
| 5,291,902 A | 3/1994 | Carman |
| 5,312,439 A | 5/1994 | Loeb |
| 5,324,316 A | 6/1994 | Schulman |
| 5,324,324 A | 6/1994 | Vachon et al. |
| 5,330,507 A | 7/1994 | Schwartz |
| 5,358,514 A | 10/1994 | Schulman |
| 5,405,367 A | 4/1995 | Schulman |
| 5,411,548 A | 5/1995 | Carman et al. | 607/138 |
| 5,417,226 A | 5/1995 | Juma |
| 5,423,329 A | 6/1995 | Ergas |
| 5,452,719 A | 9/1995 | Eisman |
| 5,484,445 A | 1/1996 | Knuth |
| 5,518,504 A | 5/1996 | Polyak |
| 5,520,606 A | 5/1996 | Schoolman et al. |
| 5,562,717 A | 10/1996 | Tippey |
| 5,569,351 A | 10/1996 | Menta et al. |
| 5,571,148 A | 11/1996 | Loeb |
| 5,611,515 A | 3/1997 | Benderev et al. |
| 5,611,768 A | 3/1997 | Tutrone |
| 5,634,462 A | 6/1997 | Tyler |
| 5,702,428 A | 12/1997 | Tippey |
| 5,752,978 A | 5/1998 | Chancellor |
| 5,807,397 A | 9/1998 | Barreras |
| 5,824,027 A | 10/1998 | Hoffer |
| 5,833,595 A | 11/1998 | Lin |
| 5,842,478 A | 12/1998 | Benderev et al. |
| 5,860,425 A | 1/1999 | Benderev et al. |
| 5,899,909 A | 5/1999 | Claren et al. |
| 5,927,282 A | 7/1999 | Lenker |
| 5,931,864 A | 8/1999 | Chastain et al. |
| 5,954,761 A | 9/1999 | Machek et al. |
| 5,957,920 A * | 9/1999 | Baker | 606/33 |
| 5,957,965 A | 9/1999 | Moumane |
| 5,978,712 A | 11/1999 | Suda et al. |
| 5,984,854 A | 11/1999 | Ishikawa |
| 6,002,964 A | 12/1999 | Feler |
| 6,026,326 A | 2/2000 | Bardy |
| 6,027,456 A | 2/2000 | Feler et al. |
| 6,039,686 A | 3/2000 | Kovac |
| 6,042,534 A | 3/2000 | Gellman et al. |
| 6,051,017 A | 4/2000 | Loeb |
| 6,055,456 A | 4/2000 | Gerber |
| 6,061,596 A | 5/2000 | Richmond |
| 6,104,955 A | 8/2000 | Bourgeois |
| 6,104,960 A | 8/2000 | Duysens |
| 6,110,101 A | 8/2000 | Tihon et al. |
| 6,131,575 A | 10/2000 | Lenker |
| 6,135,945 A | 10/2000 | Sultan |
| 6,141,594 A | 10/2000 | Flynn et al. |
| 6,161,029 A | 12/2000 | Spreigl et al. |
| 6,178,356 B1 | 1/2001 | Chastain et al. |
| 6,185,452 B1 | 2/2001 | Schulman |
| 6,208,894 B1 | 3/2001 | Schulman |
| 6,240,315 B1 | 5/2001 | Mo |
| 6,240,316 B1 | 5/2001 | Richmond |
| 6,243,607 B1 | 6/2001 | Mintchev et al. |
| 6,266,557 B1 | 7/2001 | Roe |
| 6,266,564 B1 | 7/2001 | Hill |
| 6,328,686 B1 | 12/2001 | Kovac |
| 6,341,236 B1 | 1/2002 | Osorio |
| 6,354,991 B1 | 3/2002 | Gross et al. |
| 6,360,750 B1 | 3/2002 | Gerber |
| 6,366,814 B1 | 4/2002 | Boveja |
| 6,382,214 B1 | 5/2002 | Raz et al. |
| 6,397,109 B1 | 5/2002 | Cammilli et al. |
| 6,407,308 B1 | 6/2002 | Roe |
| 6,418,930 B1 * | 7/2002 | Fowler | 128/830 |
| 6,582,441 B1 | 6/2003 | He et al. |
| 6,600,956 B2 | 7/2003 | Maschino |
| 6,612,977 B2 | 9/2003 | Staskin et al. |
| 6,641,524 B2 | 11/2003 | Kovac |
| 6,641,525 B2 | 11/2003 | Rocheleau et al. |
| 6,650,943 B1 | 11/2003 | Whitehurst |
| 6,652,449 B1 | 11/2003 | Gross et al. |
| 6,652,450 B2 | 11/2003 | Neisz et al. |
| 6,652,499 B1 | 11/2003 | Edgren et al. |
| 6,658,297 B2 | 12/2003 | Loeb |
| 6,659,936 B1 | 12/2003 | Furness |
| 6,712,772 B2 | 3/2004 | Cohen |
| 6,735,474 B1 | 5/2004 | Loeb et al. |
| 6,802,807 B2 | 10/2004 | Anderson et al. |
| 6,862,480 B2 * | 3/2005 | Cohen et al. | 607/41 |
| 6,896,651 B2 | 5/2005 | Gross et al. |
| 6,911,003 B2 | 6/2005 | Anderson et al. |
| 6,941,171 B2 | 9/2005 | Mann et al. |
| 6,952,613 B2 | 10/2005 | Swoyer et al. |
| 6,964,643 B2 | 11/2005 | Hovland et al. |
| 6,964,699 B1 | 11/2005 | Carns et al. |
| 6,971,393 B1 | 12/2005 | Mamo et al. |
| 7,079,882 B1 | 7/2006 | Schmidt |
| 7,120,499 B2 | 10/2006 | Thrope et al. |
| 7,319,905 B1 | 1/2008 | Morgan et al. |
| 7,328,068 B2 | 2/2008 | Spinelli et al. | 607/39 |
| 7,330,764 B2 | 2/2008 | Swoyer et al. |
| 7,343,202 B2 | 3/2008 | Mrva et al. |
| 7,376,467 B2 | 5/2008 | Thrope et al. |
| 7,613,516 B2 | 11/2009 | Cohen et al. |
| 7,647,113 B2 | 1/2010 | Wirbisky et al. |
| 7,771,345 B1 | 8/2010 | O'Donnell |
| 2001/0002441 A1 | 5/2001 | Boveja |
| 2001/0003799 A1 | 6/2001 | Boveja |
| 2001/0018549 A1 | 8/2001 | Scetbon |
| 2002/0022841 A1 * | 2/2002 | Kovac | 606/60 |
| 2002/0055761 A1 | 5/2002 | Mann |
| 2002/0062060 A1 * | 5/2002 | Gross et al. | 600/30 |
| 2002/0099259 A1 | 7/2002 | Anderson et al. |
| 2002/0161382 A1 | 10/2002 | Neisz et al. |
| 2002/0165566 A1 | 11/2002 | Ulmsten |
| 2003/0018365 A1 | 1/2003 | Loeb |
| 2003/0023296 A1 | 1/2003 | Osypka |
| 2003/0028232 A1 | 2/2003 | Camps et al. |
| 2003/0060868 A1 | 3/2003 | Janke et al. |
| 2003/0100930 A1 * | 5/2003 | Cohen et al. | 607/40 |

| | | | |
|---|---|---|---|
| 2003/0171644 | A1 | 9/2003 | Anderson et al. |
| 2003/0199961 | A1 | 10/2003 | Bjorklund et al. |
| 2003/0236557 | A1 | 12/2003 | Whitehurst |
| 2003/0236558 | A1 | 12/2003 | Whitehurst |
| 2004/0015057 | A1 | 1/2004 | Rocheleau et al. |
| 2004/0015204 | A1 | 1/2004 | Whitehurst |
| 2004/0015205 | A1 | 1/2004 | Whitehurst |
| 2004/0039453 | A1 | 2/2004 | Anderson et al. |
| 2004/0059392 | A1 | 3/2004 | Parramon et al. |
| 2004/0068203 | A1 | 4/2004 | Gellman et al. ............. 600/587 |
| 2004/0093053 | A1* | 5/2004 | Gerber et al. ................ 607/117 |
| 2004/0242956 | A1* | 12/2004 | Scorvo ............................ 600/30 |
| 2004/0248979 | A1 | 12/2004 | Brettman et al. ............ 514/561 |
| 2005/0038489 | A1 | 2/2005 | Grill |
| 2005/0043580 | A1 | 2/2005 | Watschke et al. |
| 2005/0065395 | A1 | 3/2005 | Mellier |
| 2005/0113877 | A1 | 5/2005 | Spinelli et al. |
| 2005/0119710 | A1 | 6/2005 | Furness et al. .................. 607/41 |
| 2005/0143618 | A1 | 6/2005 | Anderson et al. |
| 2005/0149156 | A1 | 7/2005 | Libbus et al. |
| 2005/0216069 | A1 | 9/2005 | Cohen et al. |
| 2005/0228346 | A1 | 10/2005 | Goode et al. |
| 2005/0245787 | A1 | 11/2005 | Cox et al. |
| 2005/0245874 | A1 | 11/2005 | Carrez et al. |
| 2005/0250977 | A1 | 11/2005 | Montpetit et al. |
| 2006/0004421 | A1 | 1/2006 | Bennett et al. |
| 2006/0004429 | A1 | 1/2006 | Mrva et al. |
| 2006/0149345 | A1 | 7/2006 | Boggs, II et al. |
| 2006/0241733 | A1 | 10/2006 | Zhang et al. |
| 2006/0287571 | A1 | 12/2006 | Gozzi et al. |
| 2007/0021650 | A1 | 1/2007 | Rocheleau et al. |
| 2007/0043416 | A1 | 2/2007 | Callas et al. |
| 2007/0123952 | A1 | 5/2007 | Strother et al. |
| 2007/0185541 | A1 | 8/2007 | DiUbaldi et al. ............... 607/41 |
| 2007/0239224 | A1 | 10/2007 | Bennett et al. |
| 2007/0253997 | A1 | 11/2007 | Giftakis et al. |
| 2007/0255341 | A1 | 11/2007 | Giftakis et al. |
| 2007/0260288 | A1 | 11/2007 | Gross |
| 2008/0009914 | A1 | 1/2008 | Buysman et al. |
| 2008/0071321 | A1 | 3/2008 | Boggs, II et al. |
| 2008/0132969 | A1 | 6/2008 | Bennett et al. |
| 2009/0012592 | A1 | 1/2009 | Buysman et al. |
| 2009/0043356 | A1 | 2/2009 | Longhini et al. |
| 2009/0157091 | A1 | 6/2009 | Buysman |
| 2010/0049289 | A1 | 2/2010 | Lund et al. |
| 2010/0076254 | A1 | 3/2010 | Jimenez et al. |

FOREIGN PATENT DOCUMENTS

| | | |
|---|---|---|
| EP | 0 245 547 | 5/1986 |
| EP | 1 661 600 A1 | 5/2006 |
| EP | 1119314 B1 | 6/2006 |
| GB | 2 309 388 | 7/1997 |
| JP | 52146088 | 12/1977 |
| JP | 2002521153 | 7/2002 |
| JP | 2003506145 | 2/2003 |
| JP | 2004515277 | 5/2004 |
| WO | WO 90/12617 | 11/1990 |
| WO | WO 96/04955 | 2/1996 |
| WO | 9632916 | 10/1996 |
| WO | 9817190 A2 | 4/1998 |
| WO | 0000082 A1 | 1/2000 |
| WO | 0006246 | 2/2000 |
| WO | 0019940 A1 | 4/2000 |
| WO | 0110357 | 2/2001 |
| WO | WO 02/39890 | 5/2002 |
| WO | 0245774 | 6/2002 |
| WO | WO 02/069781 | 9/2002 |
| WO | WO 02/078592 | 10/2002 |
| WO | 03002192 A1 | 1/2003 |
| WO | WO 03/002192 | 1/2003 |
| WO | WO 2006/047833 | 5/2006 |
| WO | 2007097994 A2 | 8/2007 |
| WO | 2007126632 A3 | 11/2007 |
| WO | 2007145913 A1 | 12/2007 |
| WO | 2010107751 A2 | 9/2010 |

OTHER PUBLICATIONS

International Search Report and Written Opinion of PCT/US2007/004474 filed on Feb. 22, 2007.
U.S. Appl. No. 60/779,219.
Caldwell, K.P.S. "Electrical Stimulation.", Sphincter Research Unit, Royal Devon and Exeter Hospital, Exeter (England), Urol. Int. 29: 225, 1974.(1 page).
Caldwell, K.P.S. "The Use of Electrical Stimulation in Urinary Retention and Incontinence [Abridged]." Section of Urology, vol. 61, pp. 35-39, Jul. 1968.
Caldwell, K.P.S. et al. "Urethral Pressure Recordings in Male Incontinents Under Electrical Stimulation." Investigative Urology vol. 5, No. 6, pp. 572-579, May 1968.
Caldwell, K.P.S. et al. "Stress Incontinence in Females: Report on 31 Cases Treated By Electrical Implant." J. Obstet. Gynaec. Brit. Cwlth vol. 75, pp. 777-780, Jul. 1968.
U.S. Appl. No. 60/578,742, filed Jun. 10, 2004.
U.S. Appl. No. 12/558,143, filed Sep. 11, 2009.
International Search Report and Written Opinion of PCT/US2007/000112, filed Jan. 3, 2007.
U.S. Appl. No. 61/160,765, filed Mar. 17, 2009.
Dietz et al., Mechanical Properties of Urogynecologic Implant Materials, Int. Urogynecol J. (2003) 14:239-243.
Iglesia et al., "The Use of Mesh in Gynecologic Surgery", Int. Urogynecol J. (1997) 8:105-115.
U.S. Appl. No. 11/746,476, filed May 9, 2007.
Notification of the First Office Action from corresponding Chinese patent application No. 200780007709.2, mailed Sep. 27, 2010.
Yamamoto et al., "Optimal parameters for effective electrical stimulation of the anal sphincters in a child with fecal incontinence: preliminary report," Pediatr Surg Int (1993) 8:132-137.
Yamanishi et al., "Electrical Stimulation for Stress Incontinence", Int. Urogynecol J (1998) 9:281-290 Springer-Verlag London Ltd.
Partial European Search Report from European Patent Application No. 10176162.5, mailed Jan. 21, 2011.
Search Report and Written Opinion from corresponding PCT/US2011/023677 mailed Apr. 21, 2011.
Extended European Search Report from corresponding EP 10176162.5, mailed Apr. 28, 2011.
Prosecution documents associated with U.S. Appl. No. 12/558,143 including: Restriction Requirement mailed May 12, 2011 Office Action mailed Jun. 20, 2011.
Prosecution documents associated with U.S. Appl. No. 12/295,850 including: Office Action mailed May 11, 2011.
Prosecution documents associated with U.S. Appl. No. 12/170,582 including: Final Office Action mailed Apr. 12, 2011.
Prosecution documents associated with U.S. Appl. No. 11/775,638 including: Office Action mailed Apr. 6, 2011.
Examiner's first report on Australian patent application No. 2007225322, dated Jul. 18, 2011.
Office Action from Japanese Patent Application No. 2008-557294, mailed Jan. 10, 2012.

* cited by examiner

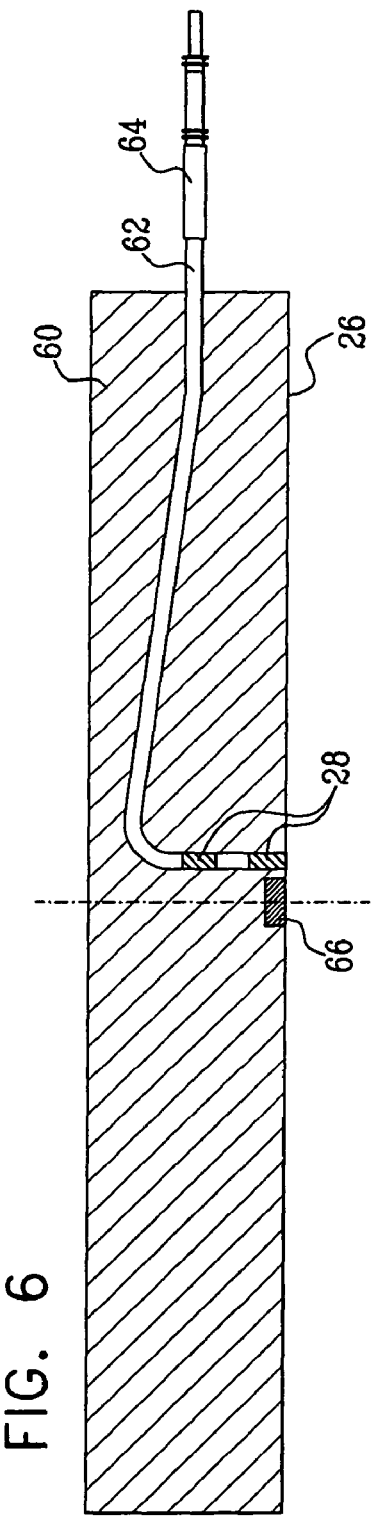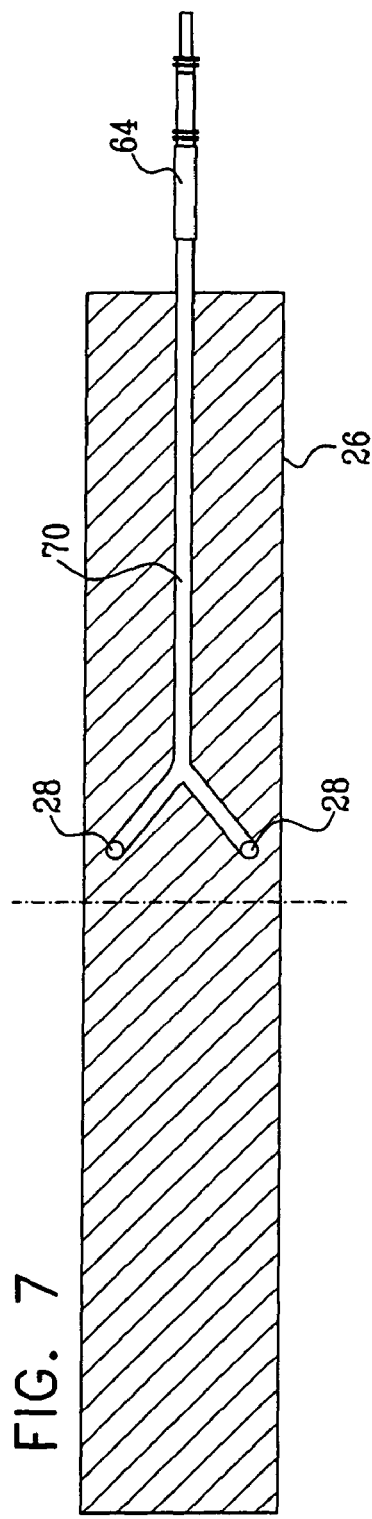

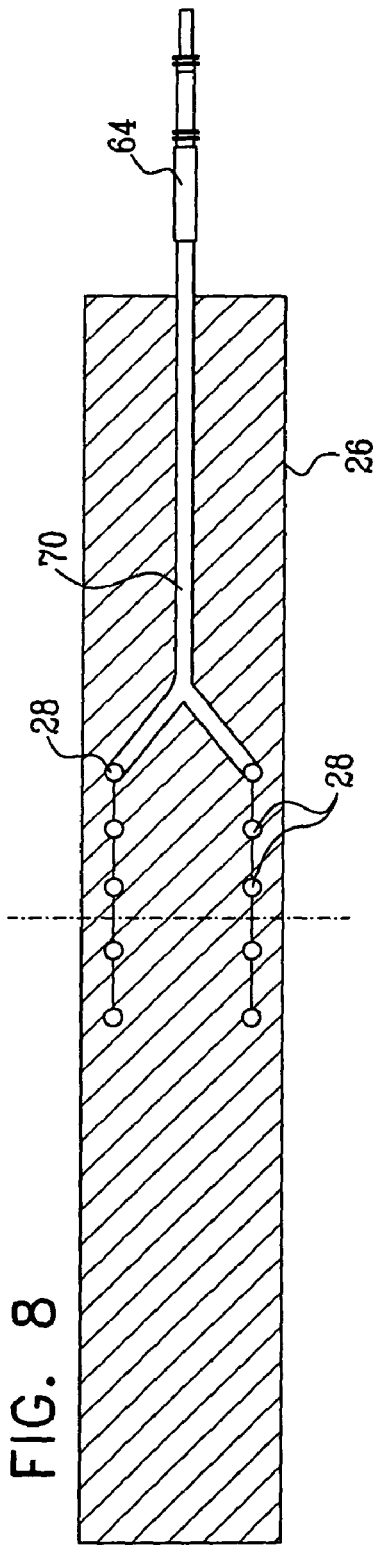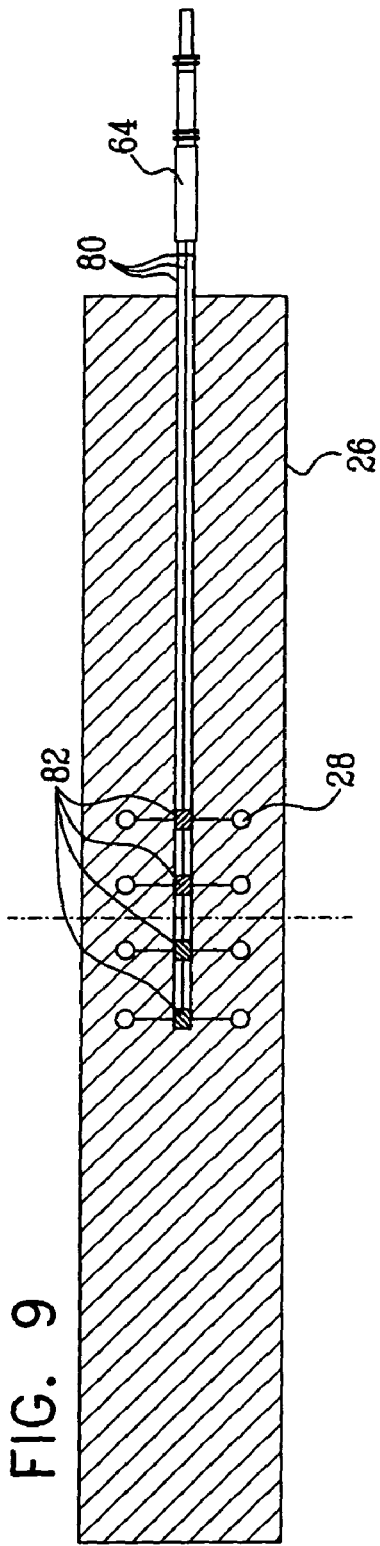

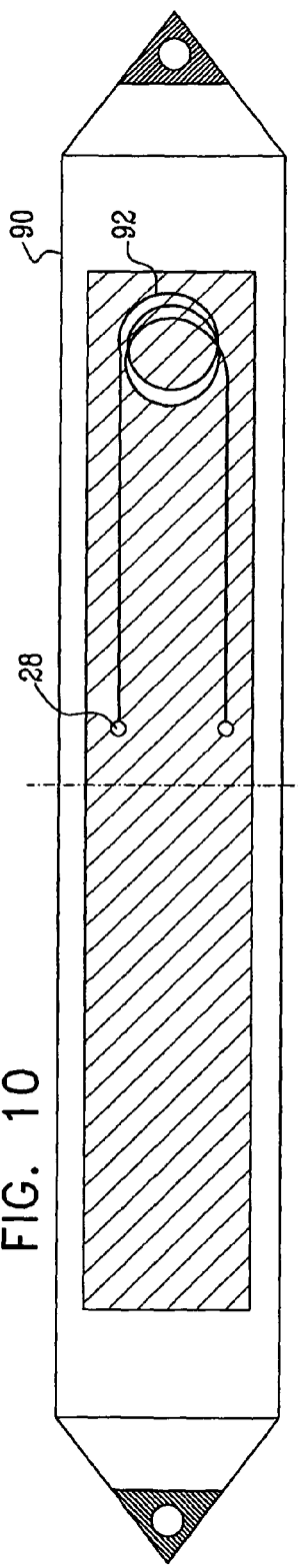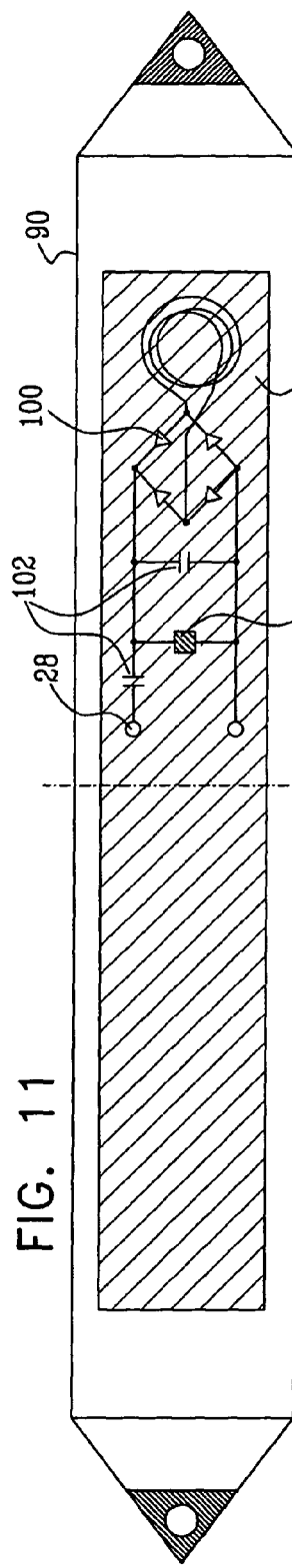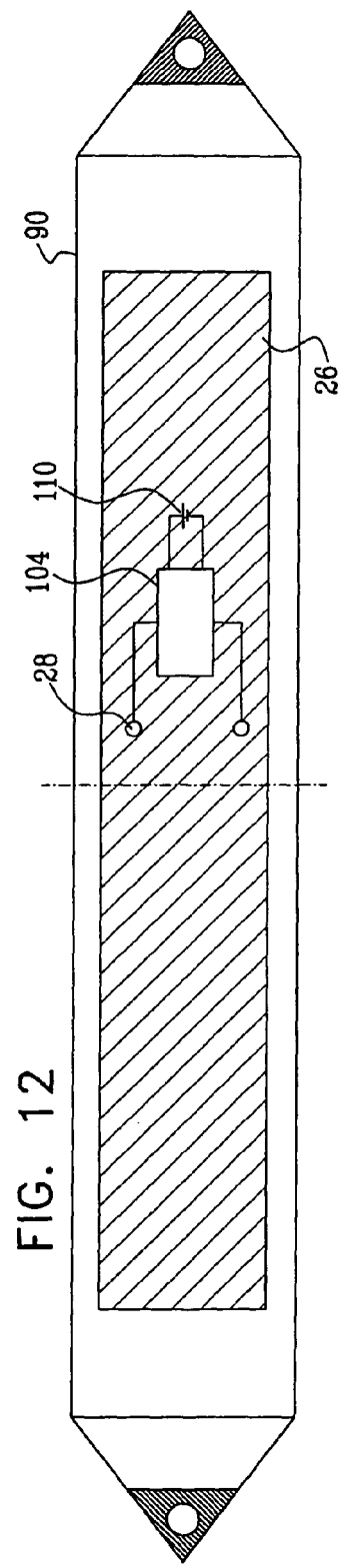

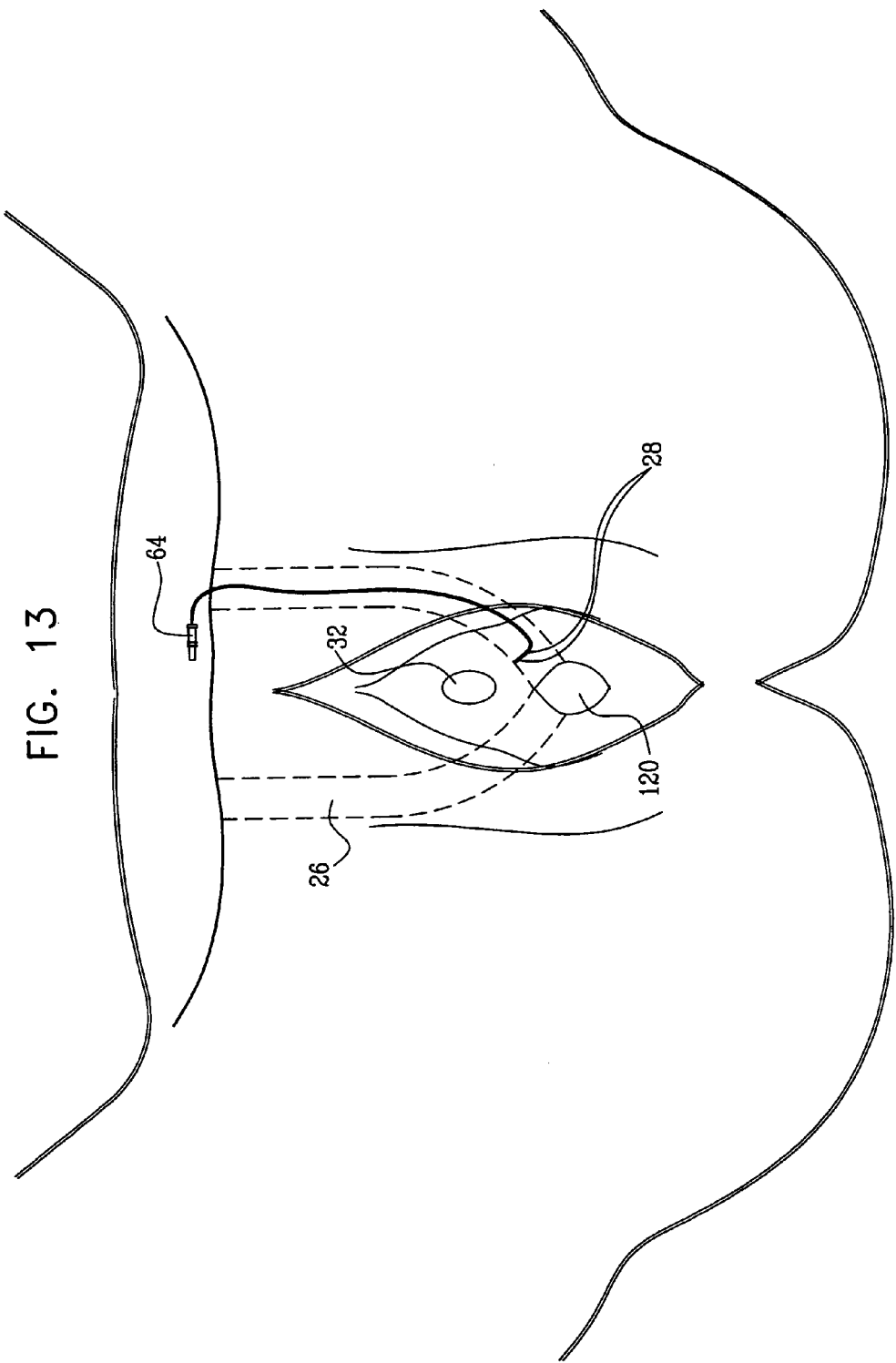

APPARATUS FOR TREATING STRESS AND URGE INCONTINENCE

CROSS-REFERENCES TO RELATED APPLICATIONS

The present patent application claims the benefit of U.S. Provisional Patent Application No. 60/779,219, entitled "SURGICAL ARTICLES AND METHODS TO TREAT STRESS AND URGE INCONTINENCE," filed Mar. 3, 2006. The content of the above-referenced application is hereby incorporated by reference in its entirety.

FIELD OF THE INVENTION

The present invention relates generally to treatment of incontinence, and specifically to implantable devices for treatment of stress and urge incontinence.

BACKGROUND OF THE INVENTION

Urinary stress incontinence is a medical condition in which sudden stress placed on a patient's bladder causes urinary incontinence. Activities such as laughing, sneezing, and lifting heavy objects frequently cause stress incontinence in susceptible patients. According to the National Institutes of Health, about 50% of all women have occasional urinary incontinence, and as many as 10% have frequent incontinence. Nearly 20% of women over age 75 experience daily urinary incontinence. Stress incontinence may occur as a result of weakened pelvic muscles that support the bladder and urethra, or because of malfunction of the urethral sphincter. Stress incontinence is often seen in women who have had multiple pregnancies and vaginal childbirths, or who have pelvic prolapse, with cystocele, cystourethrocele, or rectocele (protrusion of the bladder, urethra, or rectal wall into the vaginal space). Risk factors for stress incontinence include female sex, advancing age, childbirth, smoking, and obesity.

Urge incontinence involves a strong, sudden need to urinate, immediately followed by a bladder contraction, resulting in an involuntary loss of urine. The bladder's ability to fill and store urine requires a functional sphincter (muscle controlling output) and a stable bladder wall muscle (detrusor). Undesired bladder muscle contraction may occur as the result of a break in a neurological pathway from the brain to the bladder. It can also occur if the bladder is irritated and the normal neurological impulses to inhibit urination are insufficient to keep the bladder relaxed as it fills. Urge incontinence may result from neurological injuries (such as spinal cord injury or stroke), neurological diseases (such as multiple sclerosis), infection, bladder cancer, bladder stones, bladder inflammation, or bladder outlet obstruction.

Although urge incontinence may occur in anyone at any age, it is more common in women and the elderly. It is second only to stress incontinence as the most common cause of urinary incontinence (involuntary loss of urine), and it is common for people with stress incontinence to also have urge incontinence.

In the urology field, needles, suture passers and ligature carriers are utilized in a variety of procedures, many of which are designed to treat incontinence. A pubovaginal sling procedure is a surgical method involving the placement of a sling to stabilize or support the bladder neck or urethra. There are a variety of different sling procedures. Descriptions of different sling procedures are disclosed in U.S. Pat. No. 5,112,344 to Petros et al., U.S. Pat. No. 5,611,515 to Benderev et al., U.S. Pat. No. 5,842,478 to Benderev et al., U.S. Pat. No. 5,860,425 to Benderev et al., U.S. Pat. No. 5,899,909 to Claren et al., U.S. Pat. No. 6,039,686 to Kovac, U.S. Pat. No. 6,042,534 to Gellman et al., and U.S. Pat. No. 6,110,101 to Tihon et al., which are incorporated herein by reference and are described hereinbelow.

Some pubovaginal sling procedures extend a sling from the rectus fascia in the abdominal region, to a position below the urethra, and back again to the rectus fascia. The Tension-free Vaginal Tape (TVT) procedure (Ethicon, N.J.) utilizes a Prolene™ nonabsorbable, polypropylene mesh. Additional sling procedures are disclosed in US Patent Application Publication 2001/0018549A1 to Scetbon, and PCT Patent Publications WO 02/39890 to Ulmsten et al. and WO 02/069781 to Ulmsten et al., which are incorporated herein by reference and are described hereinbelow. Other examples of a mesh sling used for treating incontinence include the In-Fast™ and InVance™ mesh sling (American Medical Systems, Inc., Minnetonka, Minn.), which are the subject of various patents and applications. In general, these systems use bone anchors to affix the mesh sling to the pubic bone in a manner that compresses the urethra.

The BioArc™ SP Sling System and the BioArc TO Subfascial Hammock (American Medical Systems) treat female stress incontinence with a minimally invasive procedure using either a suprapubic (BioArc SP) or a transobturator (BioArc TO) approach. The BioArc utilizes a polypropylene mesh for fixation and a biologic graft material for suburethral support. Tensioning and loosening sutures maintain mesh integrity during placement and allow for intra-operative tensioning refinement without distorting the biologic graft material.

Both the BioArc SP and BioArc TO have two pieces of precut polypropylene mesh with attached clamps. The mesh and clamps are designed to facilitate the attachment of the surgeon's choice of graft materials. Tensioning and loosening sutures allow for intra-operative tension adjustment without mesh or biologic distortion. The BioArc is minimally invasive, and patients typically experience immediate continence following surgery.

The Monarc™ Subfascial Hammock™ (American Medical Systems) is a minimally invasive treatment option for female patients suffering from stress incontinence. The Monarc treats stress incontinence by supporting the urethra during abdominal stress events, such as sneezing, coughing or laughing. Monarc's outside-to-in trans-obturator approach avoids the retropubic space. A knitted, polypropylene mesh creates a hammock-shaped midurethral sling, and helps to maintain continence by supporting the midurethra during times of increased abdominal pressure. Knitted, polypropylene Type I mesh offers tissue fixation without suturing and large pores to facilitate tissue integration. The tensioning suture maintains mesh integrity during placement and allows for intra- and immediate post-operative tensioning, while reducing sling deformation. After the procedure, most patients experience immediate continence.

The SPARC™ Self-Fixating Sling System (American Medical Systems) utilizes a suprapubic approach to treat female stress incontinence due to urethral hypermobility and/or intrinsic sphincter deficiency (ISD). It utilizes a self-fixating sling with a resorbable tensioning suture that allows for intra-operative tension refinement without mesh distortion, as well as immediate post-operative adjustment prior to tissue ingrowth. The sling supports the urethra during increased abdominal pressure (e.g., sneezing, coughing or laughing). Large pores of the mesh promote tissue integration for healing. The 1.1×50 cm polypropylene mesh sling is covered with a plastic sheath, and has locking connectors attached.

SPARC's resorbable tensioning suture maintains mesh integrity during placement and allows for intra- and immediate post-operative tensioning, while reducing sling deformation. Patients typically experience immediate continence following the implantation procedure.

The In-Fast™ Ultra Transvaginal Sling (American Medical Systems) is a minimally invasive treatment for female stress incontinence. To place a sling, the In-Fast Ultra inserter is used to drive two small titanium bone screws into the posterior aspect of the pubic bone. Each screw has a suture attached that facilitates attachment to a biologic graft or synthetic mesh that is placed under the urethra, thus restoring lost pubocervical support. The graft or mesh provides support for the urethra to restore continence. The In-Fast produces immediate continence in most cases.

U.S. Pat. Nos. 6,354,991 and 6,896,651 to Gross et al., which are incorporated herein by reference, describe a device and method for treatment of urinary stress incontinence. At least one electrode is implanted in a pelvic muscle of a patient. A control unit receives signals indicative of abdominal stress in the patient and responsive thereto applies an electrical waveform to the electrode which stimulates the muscle to contract, so as to inhibit involuntary urine flow through the patient's urethra due to the stress.

U.S. Pat. No. 6,652,449 to Gross et al., which is incorporated herein by reference, describes a device for treatment of a patient's urinary incontinence, including a sensor, which generates a signal responsive to a physiological characteristic indicative of a likelihood of incontinence. A control unit receives the signal from the sensor. At least one electrode is preferably implanted in the patient. The electrode is coupled to cause contraction of the pelvic muscle of the patient responsive to application of electrical energy to the electrode. Responsive to the signal, the control unit applies an electrical waveform to the electrode, so as to inhibit the incontinence.

U.S. Pat. No. 6,862,480 to Cohen et al., which is incorporated herein by reference, describes a device for treating a medical condition. A surgical procedure for implanting the device is also disclosed. The device includes a sensor, which is adapted to generate a signal responsive to a state of a patient, and at least one electrode, which is adapted to be coupled to a pelvic site of the patient. A control unit is adapted to receive the signal, to analyze the signal so as to distinguish between an imminent stress incontinence event and an imminent urge event, and, responsive to analyzing the signal, to apply an electrical waveform to the at least one electrode. In various configurations, the device may be used alternatively or additionally to treat fecal incontinence, interstitial cystitis, chronic pelvic pain, or urine retention.

U.S. Pat. No. 6,941,171 to Mann et al., which is incorporated herein by reference, describes a method and system for treatment of incontinence, urgency, frequency, and/or pelvic pain. The method includes implantation of electrodes on a lead or the discharge portion of a catheter adjacent the perineal nerve(s) or tissue(s) to be stimulated. Stimulation pulses, either electrical or drug infusion pulses, are supplied by a stimulator implanted remotely, and through the lead or catheter, which is tunneled subcutaneously between the stimulator and stimulation site. For instance, the system and method may reduce or eliminate the incidence of unintentional episodes of bladder emptying by stimulating nerve pathways that diminish involuntary bladder contractions, improve closure of the bladder outlet, and/or improve the long-term health of the urinary system by increasing bladder capacity and period between emptying. Moreover, the system and method may allow a patient to be taught to receive one or more patterns of neural stimulation that can be prescribed by a physician and administered without continuous oversight by a clinical practitioner.

U.S. Pat. No. 6,135,945 to Sultan, which is incorporated herein by reference, describes apparatus for preventing uncontrolled discharge of urinary fluid from a patient urethra. The apparatus includes a pressure sensor operable for sensing intra-abdominal pressure when implanted in a patient and operable for generating a pressure signal in response to the sensed pressure. An actuating device is operably coupled to the pressure sensor and is responsive for generating an electrical signal in response to the pressure signal. A controller is operably coupled to the actuating device and configured for engaging the urethra to selectively compress the urethra and prevent incontinence. The controller includes a plate adapted to be positioned on one side of the urethra and an element adapted to be positioned on another side of the urethra, and is operable for varying the distance between the element and the plate in response to the electrical signal to compress the urethra therebetween so that incontinence is prevented when intra-abdominal pressure is experienced by a patient. In an embodiment, the controller is simply an electrode placed inside the wall of the urethral sphincter to enhance its contraction and tone during the increase in the intra-abdominal pressure.

In an embodiment described in the '945 patent, apparatus for preventing uncontrolled discharge of urinary fluid from a patient urethra includes (a) a pressure sensor operable for sensing intra-abdominal pressure when implanted in a patient and operable for generating a pressure signal in response to the sensed pressure; (b) an actuating device operably coupled to the pressure sensor, the actuating device responsive for generating an electrical signal in response to the pressure signal; and (c) a controller operably coupled to the actuating device and configured for engaging the urethra to selectively compress the urethra and prevent incontinence. The controller comprises a sling adapted to be positioned on one side of the urethra, a movable metal element coupled to the sling, and an electromagnetic element positioned proximate the metal element, the electromagnetic element creating a magnetic field proximate the metal element in response to the electrical signal for magnetically moving the metal element and thereby directing the sling against the urethra to compress the urethra so that incontinence is prevented when intra-abdominal pressure is experienced by a patient.

U.S. Pat. No. 5,112,344 to Petros et al., which is incorporated herein by reference, describes a method of treating female incontinence comprising looping a filamentary element between the wall of the vagina and the rectus abdominis sheath in the anterior wall of the abdomen whereby it passes to each side of the urethra into the correct spatial relationship to the pubis, allowing the development of scar tissue between the vaginal wall and the rectus abdominis sheath, and removing the filamentary element. A surgical instrument for use with the method comprises a surgical instrument for the application of a filamentary element into the body for the purpose of treating female incontinence, the instrument comprising a tubular shaft having a handle at one end and carried toward its other end a flexible needle element slidably receivable in the shaft and adapted at one end to receive a filamentary element and having an enlarged profiled portion at its other end whereby when the needle element is received in the shaft the other end of the needle element defines a convergent surface of the other end of the shaft and the one end of the needle element is exposed at the one end of the shaft.

U.S. Pat. Nos. 5,611,515, 5,842,478 and 5,860,425 to Benderev et al., which are incorporated herein by reference, describe a surgical treatment of stress urinary incontinence. The described methods include: 1) a technique of probe passage intended to avoid injuring the bladder and to provide a more accurate and reproducible capture of the pubocervical fascia lateral to the bladder neck and urethra, 2) anchor fixation of the suspending sutures to the pubic bone intended to decrease the risk of suture pull through from above and to decrease post-operative pain and 3) a technique intended to simply and reproducibly set a limited tension of the suspending sutures. A description of these methods and results of procedures with some of these methods are disclosed. Drill guides, suture passers, suture tensioners, and various related tools and devices for use in the surgical method are also described.

U.S. Pat. No. 6,039,686 to Koval, which is incorporated herein by reference, describes a pubic bone-mounted urethra stabilization and support system and method therefor for the long term cure of recurrent female urinary incontinence. The system comprises a pair of anchors affixed to the posterior/inferior pubic bone, sutures attached to the anchors, and a mesh sling passing behind and about the urethra and the adjacent endopelvic fascia and having ends attached to the anchors by the anchor-mounted sutures. The method includes the steps of accessing the urethra with the endopelvic fascia therebehind and the pubic bone, properly locating and attaching the anchors to the pubic bone, properly locating the sling about the urethra and adjacent endopubic fascia and suturing and tensioning the ends of the sling to the anchors, intending to cause the sling to restore, support and stabilize functional urethral continence anatomy and intending to prevent urethral descent under intraabdominal pressure.

U.S. Pat. No. 6,042,534 to Gellman et al., which is incorporated herein by reference, describes prefabricated urethral suspension slings, methods of making the slings, methods of attaching suture to the slings, kits comprising the slings, and methods of using the slings to treat urinary incontinence. The slings comprise a biocompatible material having an elongate shape adapted for urethral suspension. The material has a central portion extending longitudinally between a first end portion and a second end portion. Each end portion of the sling contains at least one suture receiving site. The suture receiving sites are formed prior to surgery and may be reinforced through a variety of means. Sutures may be attached to the suture receiving sites during the manufacturing process or by the physician prior to or during surgery. Additionally, the end portions of the sling containing the suture receiving sites may be thicker than the central portion of the sling.

U.S. Pat. No. 6,110,101 to Tihon et al., which is incorporated herein by reference, describes a sling for supporting the urethra and neck of the bladder to prevent urinary incontinence. The sling is intended to provide sufficient support to inhibit the unintended flow of urine, yet stretch in a controlled fashion so that the bladder can be voided at appropriate times.

US Patent Application 2001/0018549 to Scetbon, which is incorporated herein by reference, describes a device for treating urinary stress incontinence in women, including a flexible and elongate mechanism including a tape for supporting a urethra and a flat protective sheath enveloping the tape; and a puncturing needle with an active distal end and a proximal end connected to a first end of the flexible and elongate mechanism, wherein the proximal end of the puncturing needle is connected to a first end of the flexible and elongate mechanism by an intermediate traction element, a second end of the flexible and elongate mechanism being free. A method for treating urinary stress incontinence in a woman suffering from urinary stress incontinence is also described, including (a) forming an opening in an anterior vaginal wall; (b) creating, from two small suprapubic incisions formed in the abdominal wall, a right track and a left track from the abdominal skin to the opening formed in the anterior vaginal wall; (c) using a needle and an intermediate traction element to follow one of the tracks and following the other track with at least a needle; (d) verifying by cystoscopy that the paths of the tracks are outside the bladder and the urethra; (e) using a support tape surrounded by a plastic sheath to follow the tracks by passage under an inferior surface of the urethra; (f) adjusting a loop formed by the sheathed tape under the inferior surface of the urethra; (g) removing the sheath by pulling the sheath toward the outside of the woman's body through the small suprapubic incisions; and (h) leaving the tape implanted from the first to the second incision and around the urethra to support the urethra.

U.S. Pat. No. 5,899,909 to Claren et al., which is incorporated herein by reference, describes a surgical instrument and a method for treating female urinary incontinence. The instrument comprises a shank having a handle at one end thereof, and two curved needle-like elements which are connected at one end thereof, each with one end of a tape intended to be implanted into the body. These elements can be connected one at a time with the shank at the other end thereof to form a curved end portion of the shank and are intended to be passed into the body via the vagina, each element being dimensioned to extend from the inside of the vaginal wall over the back of the pubic bone to the outside of the abdominal wall. When practicing the method, the tape is passed into the body via the vagina first at one end and then at the other end, at one side and the other, respectively, of the urethra to form a loop around the urethra, located between the urethra and the vaginal wall. The tape is extended over the pubis and through the abdominal wall and is tightened. Then, the tape ends are cut at the abdominal wall, and the tape is left implanted in the body.

PCT Patent Publication WO 02/39890 to Ulmsten et al., which is incorporated herein by reference, describes a surgical instrument and a method for treating female urinary incontinence. The instrument comprises a handle mechanism and one or two curved needle-like elements which are connected at opposite ends of a length of tape, which is implanted into the body. These elements can be connected one at a time with the handle and are intended to pass into the body via the vagina, each needle-like element being dimensioned to extend from the inside of the vaginal wall, under the pubic bone and to the outside of the abdominal wall. When practicing the method, the tape is passed into the body via the vagina first at one end and then at the other end, at one side and the other, respectively, of the urethra to form a loop around the urethra, located between the urethra and the vaginal wall. The tape is extended under the pubis and through the abdominal wall and adjusted. The tape ends are cut at the abdominal wall, and the tape is left implanted in the body.

PCT Patent Publication WO 02/069781 to Ulmsten et al., which is incorporated herein by reference, describes a surgical instrument and a method for treating female urinary incontinence. A tape or mesh is permanently implanted into the body as a support for the urethra. In one embodiment, portions of the tape comprise tissue growth factors and adhesive bonding means for attaching portions of the tape to the pubic bone. In a further embodiment, portions of the tape comprise attachment means for fastening portions of the tape to fascia within the pelvic cavity. In both embodiments, the tape is implanted with a single incision through the vaginal wall.

U.S. Pat. No. 6,652,450 to Neisz et al., which is incorporated herein by reference, describes an implantable article and method of use to treat urological disorders. A biocompatible device includes a sling assembly intended to be minimally invasive and provide sufficient support to the target site. In addition, the configuration of the sling assembly is intended to allow the position of the sling to be permanently changed during and/or after implantation.

U.S. Pat. No. 6,612,977 to Staskin et al., which is incorporated herein by reference, describes an apparatus and method of use to treat urological disorders. A biocompatible device includes a handle, needle, dilator and sling assembly intended to be minimally invasive and provide sufficient support to the target site. In addition, the configuration of the sling assembly is intended to allow the sling to be adjusted during and/or after implantation.

U.S. Pat. No. 6,802,807 to Anderson et al., which is incorporated herein by reference, describes an apparatus and method of use to treat urological disorders. The device is a repositionable handle for an arcuate needle intended to be minimally invasive. The device is for use with a sling assembly that allows a sling to be controllably implanted in a position.

U.S. Pat. No. 6,911,003, US Patent Application Publication 2003/0171644 and US Patent Application Publication 2005/0143618 to Anderson et al., which are incorporated herein by reference, describe surgical articles, implants and components suitable for a transobturator surgical procedure.

US Patent Application Publication 2005/0245787 to Cox et al., which is incorporated herein by reference, describes a method of treating pelvic organ prolapse. The method generally includes the steps of establishing a first pathway between the external perirectal region of the patient to the region of the ischial spine in tissue on one side of the prolapsed organ, followed by establishing a second pathway in tissue on the contralateral side of the prolapsed organ. A support member, which includes a central support portion and two end portions, is described as being positioned in a position to reposition the prolapsed organ in the organ's anatomically correct location. The end portions of the support member are described as being introduced through the respective tissue pathways, followed by adjustment of the end portions so that the support member is located in a therapeutic relationship to the prolapsed organ that is to be supported. An apparatus and kit for the treatment is further described.

US Patent Application 2005/0250977 to Montpetit et al., which is incorporated herein by reference, describes a method for cystocele repair comprising the steps of: establishing four pathways in tissue around a bladder of a patient, introducing a strap into each of the pathways, and positioning beneath the bladder of the patient a support member having each strap connected thereto such that the bladder of the patient is supported by the support member and a bulge of the bladder into a vagina of the patient is reduced.

The following patents and published patent applications are incorporated herein by reference:

| | |
|---|---|
| U.S. Pat. No. 3,628,538 (Vincent) | U.S. Pat. No. 3,667,477 (Susset) |
| U.S. Pat. No. 3,640,284 (De Langis) | U.S. Pat. No. 3,866,613 (Kenny) |
| U.S. Pat. No. 3,646,940 (Timm) | U.S. Pat. No. 3,870,051 (Brindley) |
| U.S. Pat. No. 3,650,276 (Burghele) | U.S. Pat. No. 3,926,178 (Feldzamen) |
| U.S. Pat. No. 3,941,136 (Bucalo) | U.S. Pat. No. 4,881,526 (Johnson) |
| U.S. Pat. No. 3,983,865 (Shepard) | U.S. Pat. No. 5,013,292 (Lemay) |
| U.S. Pat. No. 3,983,881 (Wickham) | U.S. Pat. No. 5,013,292 (Lemay) |
| U.S. Pat. No. 4,023,574 (Nemec) | U.S. Pat. No. 5,019,032 (Robertson) |
| U.S. Pat. No. 4,106,511 (Erlandsson) | U.S. Pat. No. 5,082,006 (Jonasson) |
| U.S. Pat. No. 4,136,684 (Scattergood) | U.S. Pat. No. 5,094,242 (Gleason) |
| U.S. Pat. No. 4,139,006 (Corey) | U.S. Pat. No. 5,193,539 (Schulman) |
| U.S. Pat. No. 4,153,059 (Fravel) | U.S. Pat. No. 5,193,540 (Schulman) |
| U.S. Pat. No. 4,157,087 (Miller) | U.S. Pat. No. 5,199,430 (Fang) |
| U.S. Pat. No. 4,165,750 (Aleev) | U.S. Pat. No. 5,285,781 (Brodard) |
| U.S. Pat. No. 4,177,819 (Kofsky) | U.S. Pat. No. 5,291,902 (Carman) |
| U.S. Pat. No. 4,222,377 (Burton) | U.S. Pat. No. 5,312,439 (Loeb) |
| U.S. Pat. No. 4,290,420 (Manetta) | U.S. Pat. No. 5,324,316 (Schulman) |
| U.S. Pat. No. 4,387,719 (Plevnik) | U.S. Pat. No. 5,330,507 (Schwartz) |
| U.S. Pat. No. 4,406,288 (Horwinski) | U.S. Pat. No. 5,358,514 (Schulman) |
| U.S. Pat. No. 4,431,001 (Hakansson) | U.S. Pat. No. 5,405,367 (Schulman) |
| U.S. Pat. No. 4,457,299 (Cornwell) | U.S. Pat. No. 5,417,226 (Juma) |
| U.S. Pat. No. 4,492,233 (Petrofsky) | U.S. Pat. No. 5,423,329 (Ergas) |
| U.S. Pat. No. 4,515,167 (Hochman) | U.S. Pat. No. 5,452,719 (Eisman) |
| U.S. Pat. No. 4,542,753 (Brenman) | U.S. Pat. No. 5,484,445 (Knuth) |
| U.S. Pat. No. 4,568,339 (Steer) | U.S. Pat. No. 5,518,504 (Polyak) |
| U.S. Pat. No. 4,569,351 (Tang) | U.S. Pat. No. 5,520,606 (Schoolman) |
| U.S. Pat. No. 4,571,749 (Fischell) | U.S. Pat. No. 5,562,717 (Tippey) |
| U.S. Pat. No. 4,580,578 (Barson) | U.S. Pat. No. 5,571,148 (Loeb) |
| U.S. Pat. No. 4,585,005 (Lue) | U.S. Pat. No. 5,611,768 (Tutrone) |
| U.S. Pat. No. 4,602,624 (Naples) | U.S. Pat. No. 5,634,462 (Tyler) |
| U.S. Pat. No. 4,607,639 (Tanagho) | U.S. Pat. No. 5,702,428 (Tippey) |
| U.S. Pat. No. 4,628,942 (Sweeney) | U.S. Pat. No. 5,807,397 (Barreras) |
| U.S. Pat. No. 4,688,575 (DuVall) | U.S. Pat. No. 5,824,027 (Hoffer) |
| U.S. Pat. No. 4,703,755 (Tanagho) | U.S. Pat. No. 5,833,595 (Lin) |
| U.S. Pat. No. 4,731,083 (Fischell) | U.S. Pat. No. 5,927,282 (Lenker) |
| U.S. Pat. No. 4,739,764 (Lue) | U.S. Pat. No. 5,957,965 (Moumane) |
| U.S. Pat. No. 4,771,779 (Tanagho) | U.S. Pat. No. 5,984,854 (Ishikawa) |
| U.S. Pat. No. 4,785,828 (Maurer) | U.S. Pat. No. 6,002,964 (Feler) |
| U.S. Pat. No. 6,026,326 (Bardy) | U.S. Pat. No. 6,418,930 (Fowler) |
| U.S. Pat. No. 6,051,017 (Loeb) | U.S. Pat. No. 6,600,956 (Maschino) |
| U.S. Pat. No. 6,061,596 (Richmond) | U.S. Pat. No. 6,650,943 (Whitehurst) |
| U.S. Pat. No. 6,104,955 (Bourgeois) | U.S. Pat. No. 6,658,297 (Loeb) |
| U.S. Pat. No. 6,104,960 (Duysens) | U.S. Pat. No. 6,659,936 (Furness) |
| U.S. Pat. No. 6,131,575 (Lenker) | U.S. Pat. No. 6,712,772 (Cohen) |
| U.S. Pat. No. 6,135,945 (Sultan) | U.S. Pat. No. 6,735,474 (Loeb) |
| U.S. Pat. No. 6,185,452 (Schulman) | U.S. Pat. No. 01/0002441 (Boveja) |

| | |
|---|---|
| U.S. Pat. No. 6,208,894 (Schulman) | U.S. Pat. No. 01/0003799 (Boveja) |
| U.S. Pat. No. 6,240,315 (Mo) | U.S. Pat. No. 02/0055761 (Mann) |
| U.S. Pat. No. 6,240,316 (Richmond) | U.S. Pat. No. 03/0018365 (Loeb) |
| U.S. Pat. No. 6,266,557 (Roe) | U.S. Pat. No. 03/0018365 (Loeb) |
| U.S. Pat. No. 6,266,564 (Hill) | U.S. Pat. No. 03/0236557 (Whitehurst) |
| U.S. Pat. No. 6,341,236 (Osorio) | U.S. Pat. No. 03/0236558 (Whitehurst) |
| U.S. Pat. No. 6,360,750 (Gerber) | U.S. Pat. No. 04/0015204 (Whitehurst) |
| U.S. Pat. No. 6,366,814 (Boveja) | U.S. Pat. No. 04/0015205 (Whitehurst) |
| U.S. Pat. No. 6,407,308 (Roe) | U.S. Pat. No. 04/0059392 (Parramon) |

SUMMARY OF THE INVENTION

In some embodiments of the present invention, pelvic treatment apparatus comprises an implantable mechanical support, such as a sling, that is shaped to support a portion of a urethra of a patient or another pelvic structure. One or more electrodes are coupled to the mechanical support, so as to contact tissue of the patient. A control unit drives the electrodes to apply a current to the tissue. The mechanical support is typically configured to treat stress incontinence or another condition in which it is desired to support the urethra, and the applied current is typically configured to treat urge incontinence.

For some applications, the current is configured to stimulate a pelvic muscle of the patient and induce contraction of the muscle. Alternatively or additionally, the current induces action potential propagation in a nerve of the patient, thereby inducing contraction of a pelvic muscle of the patient. Further alternatively or additionally, the current induces action potential propagation that induces relaxation of a pelvic muscle of the patient.

It is known that many patients develop stress incontinence prior to developing urge incontinence. In many cases, at the time of implantation of the apparatus provided by these embodiments, the patient does not have a condition such as urge incontinence or another condition designated for treatment by the current. Nevertheless, the apparatus is ready for treatment of the condition should it develop. The current is typically not applied on a regular basis (e.g., for 30 consecutive days) in the absence of a medical indication for applying the current, although it may be applied intermittently to confirm that the electrodes are properly aligned, that the batteries are operational, or for another testing purpose.

For some applications (e.g., as a cost saving measure), the mechanical support coupled to the electrodes is implanted so that the mechanical support can treat stress incontinence, while the control unit is implanted at a later date if the patient develops urge incontinence or another condition designated for treatment by the current.

There is therefore provided, in accordance with an embodiment of the invention, apparatus including:

an implantable mechanical support, shaped to support a portion of a urethra of a patient;

one or more electrodes, coupled to the mechanical support, so as to contact tissue of the patient when the mechanical support is implanted in the patient; and a control unit, operative to drive the electrodes to apply a current to the tissue.

In an embodiment, the mechanical support is shaped to define a longitudinal axis thereof, and wherein all of the electrodes are greater than 2 mm from a center point of the longitudinal axis.

In an embodiment, the control unit is operative to configure the current to stimulate a pelvic muscle of the patient and induce contraction of the muscle.

In an embodiment, the control unit is operative to configure the current to induce in a nerve of the patient action potential propagation that induces contraction of a pelvic muscle of the patient.

In an embodiment, the control unit is operative to configure the current to induce in a nerve of the patient action potential propagation that induces relaxation of a pelvic muscle of the patient.

In an embodiment, the mechanical support includes a sling.

In an embodiment, the mechanical support includes an electrode lead, and wherein the electrode lead couples the control unit to at least one of the electrodes.

In an embodiment, the mechanical support includes an injectable agent adapted to solidify following implantation thereof in the patient.

In an embodiment, the mechanical support includes an injectable agent selected from the group consisting of: polytetrafluoroethylene, silicone, autologous fat, and collagen.

In an embodiment, the mechanical support includes a plurality of beads selected from the group consisting of: carbon beads, and polymer beads.

In an embodiment, the mechanical support includes an injectable scarring agent suitable for treating stress incontinence by tightening a pelvic tissue structure of the patient.

In an embodiment, the mechanical support includes an inflatable balloon.

In an embodiment, the mechanical support is adapted to be implanted in the patient via an approach selected from the group consisting of: a suprapubic approach, a transvaginal approach, a retropubic approach, and a transobturator approach.

In an embodiment, the mechanical support is adapted to be implanted in the patient at least in part at an intraurethral site of the patient.

In an embodiment, the control unit is wirelessly coupled to the one or more electrodes.

In an embodiment, the control unit is operative to wirelessly drive the electrodes from a site outside of a body of the patient.

In an embodiment, the control unit is operative to wirelessly drive the electrodes from a site within a body of the patient.

In an embodiment, the mechanical support includes a longitudinal element that is round in cross-section and is sized to support the portion of the urethra.

In an embodiment, a diameter of the longitudinal element is between 2 and 5 mm.

In an embodiment, the longitudinal element includes a suture.

In an embodiment, the longitudinal element includes a plastic tube.

In an embodiment, the mechanical support includes an inflatable tube.

In an embodiment, the mechanical support includes a drug, operative to be released from the mechanical support after implantation in the patient.

In an embodiment, the apparatus includes a pump operative to pump the drug from the mechanical support.

In an embodiment, the control unit includes a drug, operative to be released from the control unit after implantation in the patient.

In an embodiment, the apparatus includes a pump operative to pump the drug from the control unit.

In an embodiment, the one or more electrodes include three or more electrodes, and wherein the control unit is adapted to operate in a mode in which it drives current through a subset of the electrodes, in response to a designation, with respect to the subset of the electrodes, generated following implantation of the mechanical support.

In an embodiment, the control unit is operative to perform a calibration procedure in which it (a) applies the current to a plurality of subsets of the electrodes at different times, and (b) receives the designation in response to a physiological response of the patient to (a).

In an embodiment, the control unit is operative to configure the current to be suitable for treating a condition of the patient selected from the group consisting of: urge incontinence, bladder dysfunction, mixed incontinence, overactive bladder, interstitial cystitis, and fecal incontinence.

In an embodiment, the control unit is operative to set an amplitude of the current to be insufficient to induce contraction of a pelvic muscle of the patient, and sufficient to induce relaxation of a bladder muscle of the patient.

In an embodiment, the control unit is operative to set an amplitude of the current to be less than 4 volts.

In an embodiment, the control unit is operative to set a frequency of the current to be between 5 and 15 Hz.

In an embodiment, the control unit is operative to set a duration of pulses of the current to be between 50 us and 1 ms.

In an embodiment, the control unit is operative to apply the current as a series of pulse trains, each pulse train lasting between 2 and 8 seconds.

In an embodiment, the control unit is operative to apply the current as a series of pulse trains, a time between each pulse train being between 10 and 20 seconds.

In an embodiment, the control unit is operative to drive the electrodes to apply the current independently of any sensing of an imminent event of the selected condition.

In an embodiment, the apparatus does not include any sensors indicative of a physiological state of the patient.

In an embodiment, the control unit is operative to configure the current to be suitable for treating stress incontinence.

In an embodiment, the apparatus includes a sensor operative to generate a signal indicative of imminent stress incontinence.

In an embodiment, the control unit is operative to set an amplitude of the current to be greater than 4 volts.

In an embodiment, the control unit is operative to set a pulse duration of pulses of the current to be greater than 1 ms.

In an embodiment, the control unit is operative to increase an amplitude of pulses of the current from a first amplitude to a second amplitude.

In an embodiment, the control unit is operative to set the first amplitude to be less than 4 volts.

In an embodiment, the control unit is operative to set the second amplitude to be greater than 4 volts.

In an embodiment, the control unit is operative to increase a pulse duration of pulses of the current from a first pulse duration to a second pulse duration.

In an embodiment, the first pulse duration is less than 500 us.

In an embodiment, the second pulse duration is greater than 500 us.

There is also provided, in accordance with an embodiment of the invention, a method, including:

implanting a mechanical support in a patient;

mechanically supporting, with the mechanical support, a portion of a urethra of the patient; and driving a current from a site of the mechanical support into tissue of the patient.

In an embodiment, driving the current includes driving the current from a plurality of sites which are aligned around less than 180 degrees of the urethra.

In an embodiment, mechanically supporting includes treating stress incontinence of the patient.

In an embodiment, mechanically supporting includes treating cystocele of the patient.

In an embodiment, mechanically supporting includes treating pelvic organ prolapse of the patient.

In an embodiment, the method includes releasing a drug from the mechanical support.

In an embodiment, releasing the drug includes pumping the drug from the mechanical support.

In an embodiment, the method includes releasing a drug from a drug-release site other than the mechanical support.

In an embodiment, releasing the drug includes pumping the drug from the drug-release site.

In an embodiment, driving the current includes driving the current independently of any sensing of an imminent event of the selected condition.

In an embodiment, the method includes at a pre-implantation time prior to a first time of mechanically supporting the portion of the urethra, identifying the patient as not suffering from urge incontinence; and at a post-implantation time subsequent to the first time of mechanically supporting the portion of the urethra, identifying the patient as suffering from urge incontinence, wherein driving the current includes:

not driving the current on each of any 30 consecutive days prior to the post-implantation time; and driving the current on each of at least 30 consecutive days following the post-implantation time.

In an embodiment, the method includes implanting a control unit for driving the current greater than 30 days following a first time of mechanically supporting the portion of the urethra.

In an embodiment, driving the current includes starting to drive the current on each of at least 30 consecutive days at a time greater than 60 days from a first time of mechanically supporting the portion of the urethra.

In an embodiment, driving the current includes configuring the current to treat at least one condition, the at least one condition including a condition that is not stress incontinence.

In an embodiment, the method includes configuring the current to be suitable for treating stress incontinence.

There is further provided, in accordance with an embodiment of the invention, apparatus for treating a patient, including:

an implantable mechanical support, shaped to (a) support a urethra of a patient, (b) define one or more pockets, such that the pockets are not under the urethra when the mechanical support is disposed in the patient in a urethra-supporting position, and (c) define one or more channels of the mechanical support providing fluid communication between the pockets and a region of the mechanical support that is under the urethra when the mechanical support is in the urethra-supporting position; and a substance disposed within the pockets, and operative to flow from the pockets to the region of the mechanical support under the urethra in response to increased pelvic pressure, and to return to the pockets when the pelvic pressure decreases.

There is yet further provided, in accordance with an embodiment of the invention, a method for treating a patient, including:

implanting a mechanical support in a position that supports a urethra of a patient; and in response to increased pelvic pressure of the patient, moving a substance stored in a portion of the mechanical support that is not under the urethra to a portion of the mechanical support that is under the urethra.

The present invention will be more fully understood from the following detailed description of embodiments thereof, taken together with the drawings, in which:

BRIEF DESCRIPTION OF THE DRAWINGS

FIGS. 2-12 are schematic illustrations of mechanical supports of the pelvic treatment apparatus of FIG. 1, in accordance with respective embodiments of the present invention;

FIGS. 13-15 are schematic illustrations of the pelvic treatment apparatus of FIG. 1 implanted in a female patient, in accordance with respective embodiments of the present invention;

DETAILED DESCRIPTION OF EMBODIMENTS

Figure 1:
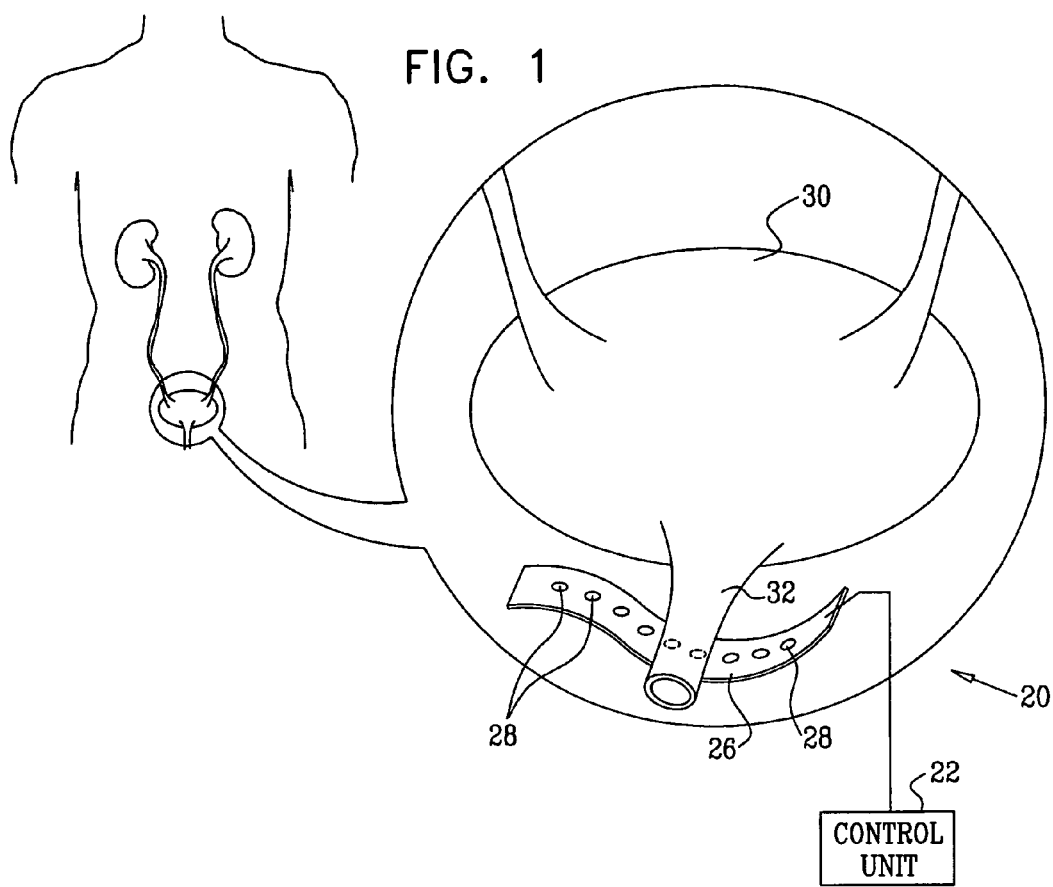
FIG. 1 is a schematic illustration of pelvic treatment apparatus coupled to the urethra of a patient, in accordance with an embodiment of the present invention.

In some embodiments of the present invention, pelvic treatment apparatus 20 comprises an implantable mechanical support 26, such as a mesh or non-mesh sling, that is shaped to support and/or compress a portion of a urethra 32 of a patient or another pelvic structure. One or more electrodes 28 are coupled to mechanical support 26, so as to contact tissue of the patient. A control unit 22 inside or outside of the patient's body drives electrodes 28 to apply a current to the tissue. The mechanical support is typically configured to treat stress incontinence or another condition in which it is desired to support the urethra, and the applied current is typically configured to treat urge incontinence.

For some applications, the current is configured to stimulate a pelvic muscle of the patient and induce contraction of the muscle in order to, for example, tighten a sphincter muscle. (Suitable parameters for such muscle stimulation are described, for example, in patent references in the Background section of the present patent application that relate to treating urge and/or stress incontinence.)

Alternatively or additionally, the current induces action potential propagation in a nerve of the patient, thereby inducing contraction of a pelvic muscle of the patient. (Suitable parameters for such nerve stimulation are described, for example, in patent references in the Background section of the present patent application that relate to treating urge and/or stress incontinence.)

Further alternatively or additionally, the current induces action potential propagation that induces relaxation of a pelvic muscle of the patient. Suitable parameters for such nerve stimulation are described, for example, in patent references in the Background section of the present patent application that relate to treating urge and/or stress incontinence. In an embodiment, an amplitude of the current is set to be insufficient to induce contraction of a pelvic muscle of the patient, but sufficient to induce relaxation of a bladder muscle of the patient. In an embodiment, the amplitude is less than 4 volts. For example, a series of pulse trains may be applied generally continuously, each pulse train having an amplitude of about 3 volts and a duration of about 5 seconds, and being separated from the next pulse train by about 16 seconds. The pulse trains comprise square pulses at about 10 Hz, whose pulse durations may range from about 50 us to about 1 ms. The actual pulse duration used is typically determined during a calibration procedure so as to attain maximal effect without patient sensation of the applied signal (or significant patient sensation of the signal). The current is typically applied independently of any sensing of an imminent event of urge incontinence, and may, for example, be applied throughout the day and night. Additionally, apparatus 20 in some embodiments does not comprise any sensors indicative of a physiological state of the patient.

By way of illustration and not limitation, techniques believed by the inventor to be particularly suitable for the described muscle and/or nerve stimulation are described in U.S. Pat. Nos. 6,354,991, 6,896,651, and 6,652,449 to Gross et al., U.S. Pat. No. 6,862,480 to Cohen et al., and U.S. Pat. No. 6,941,171 to Mann et al., which are incorporated herein by reference. In an embodiment, control unit 22 comprises circuitry used to drive the InterStim™ (Medtronic, Inc.).

In an embodiment, control unit 22 is configured to drive electrodes 28 to treat stress incontinence of the patient, in addition to or instead of treating urge incontinence. Typically, in response to a detection of imminent stress incontinence (e.g., via pressure and/or electromyographic measurements), control unit 22 applies a train of pulses that start with an approximately 3 volt, 50 us pulse and grow rapidly and generally monotonically to an approximately 6 volt, 2 ms pulse. Each pulse is separated by about 25 ms from the previous pulse. Typically, the total time for the train of pulses to grow to the 6 volt level is about 50-250 ms, or about 250-1500 ms.

For some applications control unit 22 comprises very simple circuitry, suitable for applying a single non-varying waveform. Alternatively, the control unit is programmable, e.g., wirelessly under physician control, in order to optimize stimulation parameters following implantation. The control unit typically comprises a rechargeable battery, and the patient is instructed to recharge the battery as necessary (e.g., nightly or weekly). Alternatively, the control unit comprises a long-life battery, which is replaced every few years.

Mechanical support 28 may be configured for implantation by any of a number of known surgical approaches, for example, a suprapubic approach, a transvaginal approach, a retropubic approach, and a transobturator approach. Techniques for implanting a mechanical support via these approaches and others are well known in the art, and are described, for example, in many of the references cited in the Background section of the present patent application. Regardless of the particular approach selected, mechanical support 26 (when it is generally sling-type) and electrodes 28 are typically aligned around less than 180 degrees of the urethra, as shown in FIG. 1.

Mechanical support 26 is shown in the figures as being generally ribbon shaped, by way of illustration and not limitation. The scope of the present invention includes shaping mechanical support 26 to be round in cross-section, or to have another shape in cross-section, as well. In an embodiment, the mechanical support and/or the electrodes are implanted intraurethrally, at least in part.

For some applications, the mechanical support comprises a drug which is slowly eluted therefrom following implantation (e.g., in order to reduce pain or inflammation, or to increase adhesion of the support to surrounding tissue). Alternatively or additionally, the control unit comprises a drug reservoir and, for some applications, a pump that pumps the drug from the reservoir into tissue of the patient. In an embodiment, the drug is pumped from the reservoir into the tissue via the mechanical support.

For some applications, only one electrode 28 is coupled to mechanical support 26, and another electrode is provided, for example, by a conductive case of control unit 22. Alternatively, two electrodes 28 are coupled to mechanical support 26. In an embodiment, pelvic treatment apparatus 20 comprises three or more electrodes 28 (as shown in the figures), and control unit 22 drives current through the three or more electrodes as part of a treatment protocol for urge incontinence or another condition.

Typically, when mechanical support 26 comprises three or more electrodes, only a subset of these electrodes optimally treat the condition, while others of these electrodes are not well positioned to optimally treat the condition. Because of the practical realities of some implantation procedures, it is not easy to know in advance which of the electrodes will be optimally placed. In these cases, control unit 22 typically receives, following implantation of the mechanical support, a designation of the particular subset of electrodes, and drives current through the subset of the electrodes in response to the designation. For example, the control unit may perform a calibration procedure in which it (a) applies the current to all of the electrodes, and (b) receives the designation from the physician based on the extent to which the current applied through each electrode achieved a desired response (e.g., relief of an urge symptom due to relaxation of bladder 30).

In an embodiment, electrodes 28 are movable by the physician during the implantation procedure in order to allow them to be advantageously positioned for applying the current to the tissue.

Figure 2:
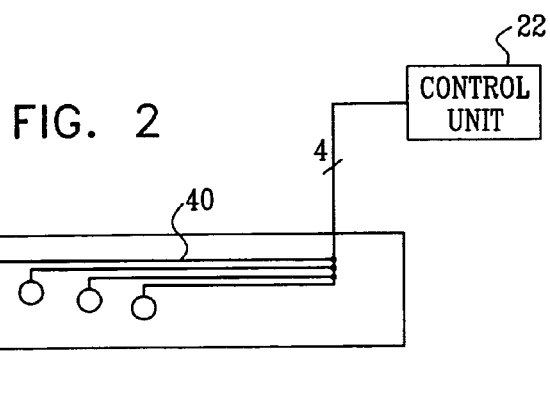

FIG. 2 is a schematic illustration of mechanical support 26, in accordance with an embodiment of the present invention. Each electrode is integrated into the body of the mechanical support, e.g., by being stitched thereto or attached thereto with an adhesive. As appropriate, the electrodes may protrude from the mechanical support or be flush with the mechanical support, and may establish electrical contact with tissue on one or both sides of the mechanical support.

Electrode leads 40 couple electrodes 28 to control unit 22. For some applications, the leads themselves form the mechanical support, without a distinct separate mechanical support like a sling as is known in the art. For ease of handling the leads, the leads may in any case be incorporated into a single supporting body (e.g., as shown in FIG. 2), even if the supporting body does not provide the majority of the support of the pelvic structure.

It is noted that although the figures show a sling providing support to urethra 32, this is by way of illustration and not limitation. The scope of the present invention includes coupling electrodes 28 to other mechanical supports, as well. For example, as described, the mechanical support may comprise one of electrode leads 40. Alternatively, the mechanical support comprises:

- one or more thick sutures or other round longitudinal elements sized to support the portion of the urethra (e.g., 2-5 mm in diameter);
- a plastic or inflatable tube, sized to support the portion of the urethra (such as the type manufactured by American Medical Systems for penile implants);
- an injectable agent adapted to solidify into a generally homogenous structure following implantation thereof in the patient. Suitable materials for injection into a patient to treat stress incontinence include polytetrafluoroethylene (Teflon), silicone, autologous fat, and collagen;
- carbon or polymer beads that in combination support the urethra;
- an injectable scarring agent (e.g., sodium tetradecyl sulfate (Sotradecol)) suitable for treating stress incontinence by tightening a pelvic tissue structure of the patient; and/or
- an inflatable balloon.

In some embodiments, mechanical support 26 is placed within an orifice of the patient's body. In other words, in these embodiments the mechanical support is not implanted in the patient. For example, mechanical support 26 may comprise a pessary, which treats stress incontinence by pressing urethra 32 against the upper posterior portion of the symphysis pubis and elevating the bladder neck. As appropriate, techniques and apparatus described in U.S. Pat. No. 3,866,613 to Kenny or U.S. Pat. No. 6,418,930 to Fowler may be utilized in carrying out these embodiments of the present invention.

Control unit 22 is shown in FIG. 22 as being separate from mechanical support 26. In an embodiment, the control unit is not implanted at the same time as mechanical support 26 in cases where the patient does not suffer from a condition designated for treatment by current applied through electrodes 28. If the patient later develops such a condition (e.g., urge incontinence), then the control unit is implanted at that time and coupled to the mechanical support.

Figure 3:
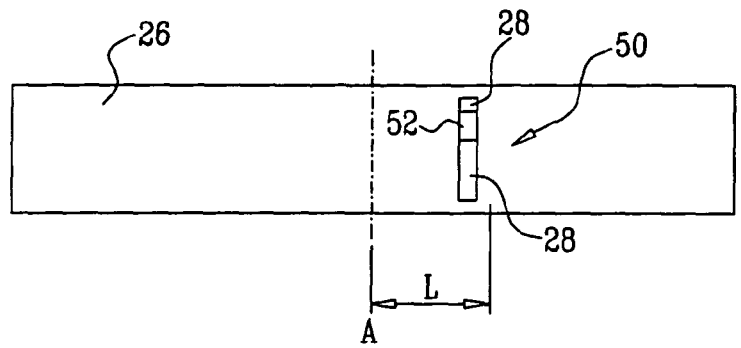

FIG. 3 is a schematic illustration of mechanical support 26, in accordance with another embodiment of the present invention. In this embodiment, a control unit 52 is integrated into the mechanical support. For example, control unit 52 and electrodes 28 may be incorporated in a single integrated unit, as shown in FIG. 3. In an embodiment, the single integrated unit comprises a BION™ (Advanced Bionics Corp.) or similar device.

The electrodes and control unit 52 may be located at the center of mechanical support 26 (designated by "A" in the figure), but are typically disposed at least a distance L of 2 mm from the center, for example between about 2 and about 6 mm.

Figure 4:
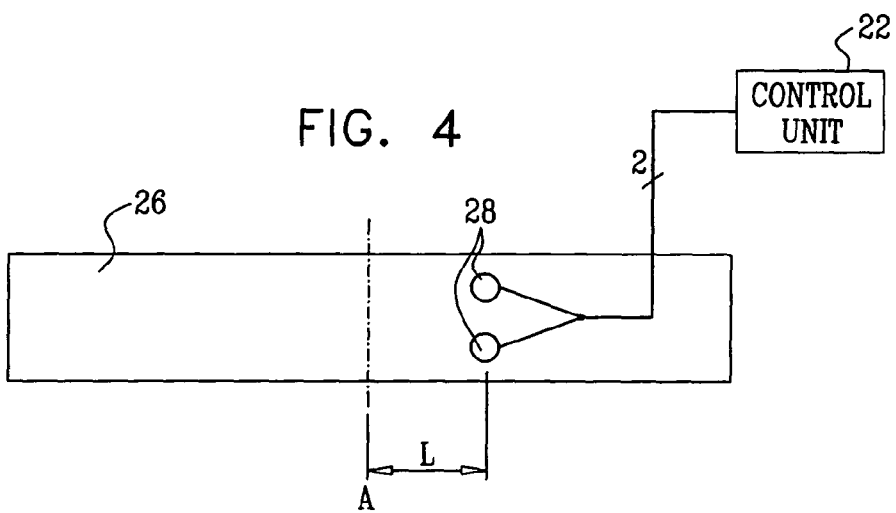

FIG. 4 is a schematic illustration of mechanical support 26, in accordance with yet another embodiment of the present invention. In this embodiment, electrodes 28 are located at the distance L from the center of mechanical support 26, and control unit 22 is coupled to the mechanical support via electrode leads.

Figure 5:
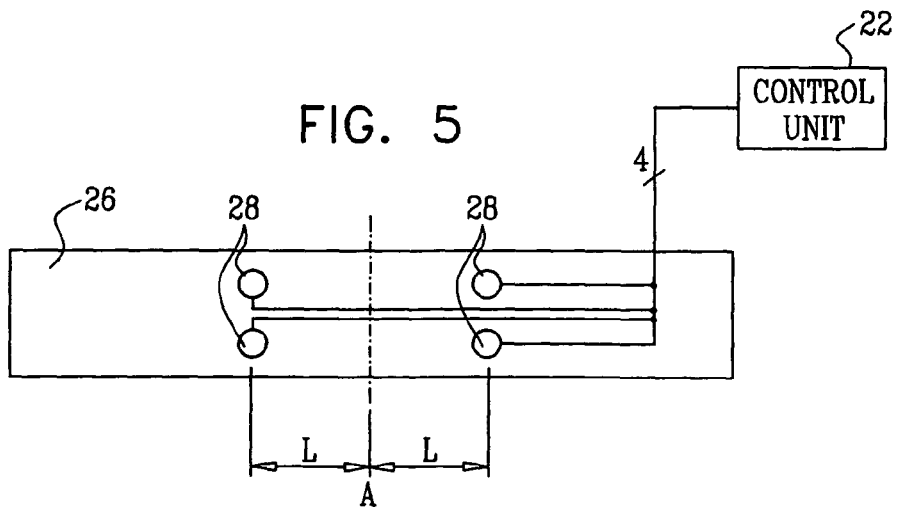

FIG. 5 is a schematic illustration of mechanical support 26 in accordance with still another embodiment of the present invention, in which electrodes 28 are located on either side of the center of the mechanical support, in order to provide bilateral stimulation of pelvic tissue.

FIG. 6 is a schematic illustration of mechanical support 26, in accordance with an embodiment of the present invention. In this embodiment, a lead 62 having electrodes 28 at a distal end thereof is coupled to mechanical support 26 by an adhesive, sutures, or other coupling mechanism that would be obvious to a person of ordinary skill in the art having read the disclosure of the present patent application. A connector 64 (e.g., an IS-1 connector) couples electrodes 28 to control unit 22 (not shown).

For some applications, a mark 66 on mechanical support 26 indicates the center point (or another point of interest) of mechanical support 26, and is visible to the physician implanting the mechanical support during the implantation procedure, to facilitate proper placement of the mechanical support and/or electrodes.

Reference is now made to FIGS. 7 and 8, which are schematic illustrations of mechanical support 26, in accordance with respective embodiments of the present invention. In FIG. 7, an electrode lead 70 is printed on mechanical support 26, and allows control unit 22 to drive a current between two electrodes 28 through tissue of the patient. In FIG. 8, printed electrode lead 70 couples control unit 22 to a larger number of electrodes 28, which may be individually addressable or addressable as groups (e.g., to drive current between the upper and lower sets of electrodes).

FIG. 9 is a schematic illustration of mechanical support 26, in accordance with an embodiment of the present invention. Mechanical support 26 is coupled to control unit 22 (not shown) via a lead having a plurality of wires 80. One or more circuitry units 82 on mechanical support 26 direct current from the control unit to selected subsets of electrodes 28. For example, each circuitry unit 82 may comprise a multiplexer, a microchip, or a decoder, and may be configured to interpret a digital signal on wires 80 that indicates which of electrodes 28 is to be activated at a given time.

Reference is now made to FIGS. 10 and 11 which are schematic illustrations of mechanical support 26 packaged within a low friction casing 90, in accordance with an embodiment of the present invention. Typically, mechanical support 26 and casing 90 are placed within the patient's body during an implantation procedure, and casing 90 is removed after the mechanical support is in place. In the embodiment shown in FIG. 10, a coil 92 is coupled to electrodes 28, and is inductively driven by an internal or external control unit 22 to apply a current to electrodes 28. In FIG. 11, the current in coil 92 is regulated by various components, such as diodes 100, capacitors 102, and a load 104, before being driven between electrodes 28.

FIG. 12 is a schematic illustration of mechanical support 26, in accordance with another embodiment of the present invention. In this embodiment, a microchip 104 and a rechargeable or non-rechargeable battery 110 are fixed to mechanical support 26, and drive current between electrodes 28.

FIG. 13 is a schematic illustration of pelvic treatment apparatus 20, comprising mechanical support 26, electrodes, 28, and a lead coupling the electrodes to connector 64, prior to placement of control unit 22 in a position for driving current through the electrodes, in accordance with an embodiment of the present invention. For some applications, a patient who has stress incontinence but does not have urge incontinence has the apparatus shown in FIG. 13 implanted, and the control unit is not implanted. If the patient later develops urge incontinence, then control unit 22 is implanted, as described hereinbelow with reference to FIG. 15.

Figure 14:
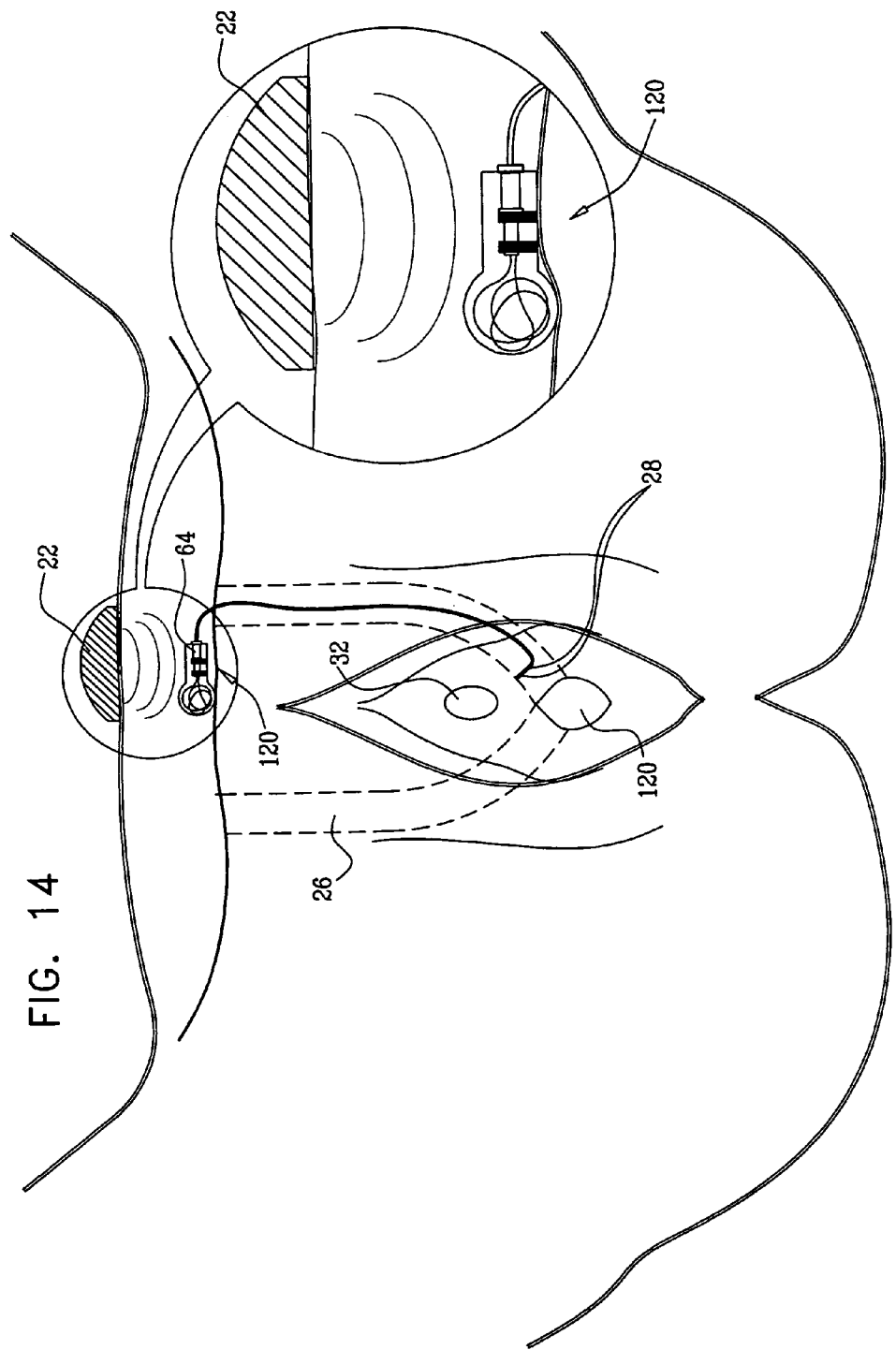
Figure 15:
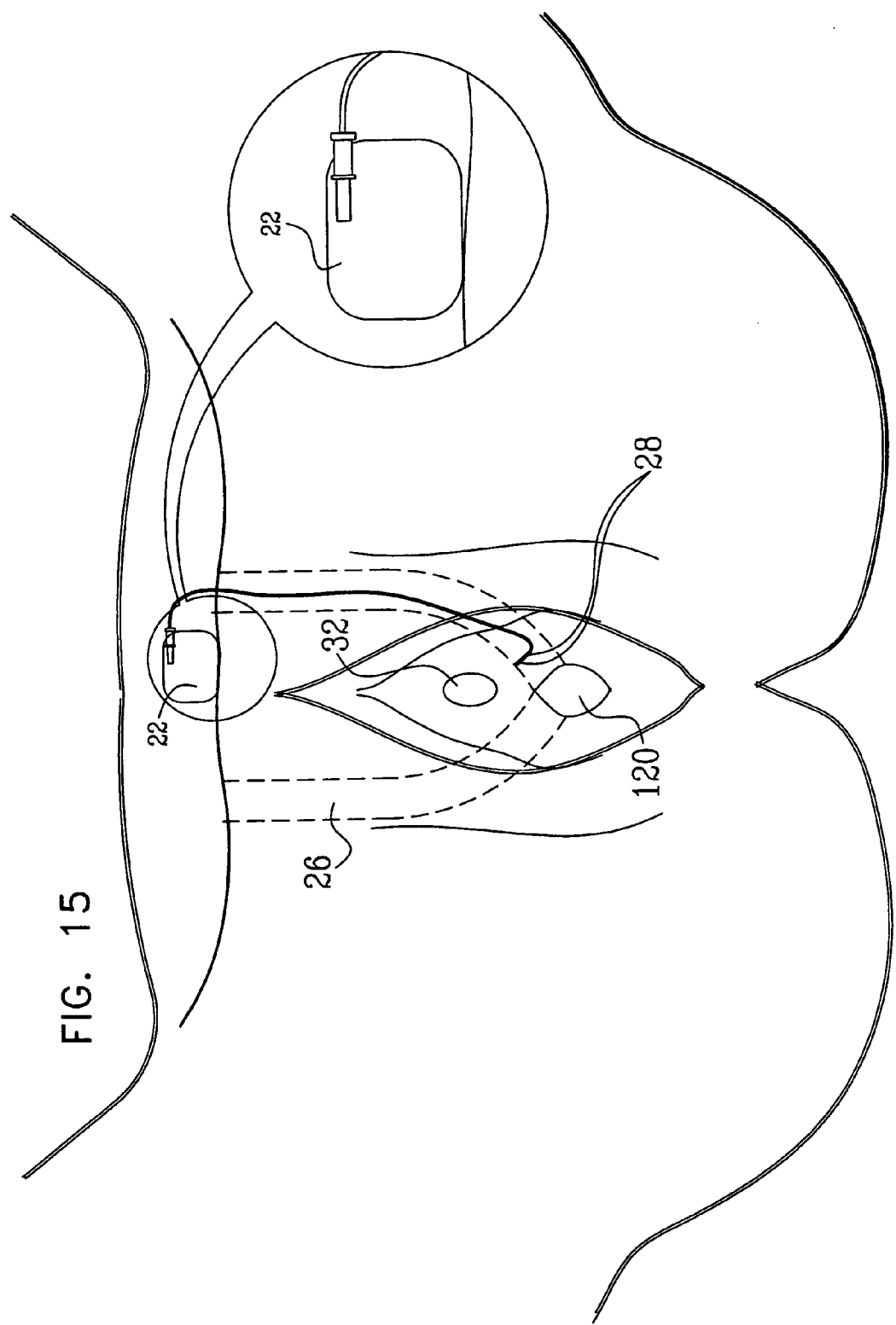

Reference is now made to FIGS. 14 and 15, which are schematic illustrations of pelvic treatment apparatus 20, comprising mechanical support 26, electrodes 28, and a lead coupling the electrodes to connector 64, in accordance with an embodiment of the present invention. In the embodiment shown in FIG. 14, a wireless receiver 120 is coupled to mechanical support 26, either via connector 64 (as shown), or as described hereinabove with reference to FIG. 10 or 11. For some applications, a patient who has stress incontinence but does not have urge incontinence has the apparatus shown in FIG. 14 implanted, excluding control unit 22. If, at a later time, the patient develops urge incontinence, then an external control unit 22 is placed in a position to wirelessly drive current through electrodes 28. If the current application treats the urge incontinence, then, typically, an implantable control unit 22 is placed within the patient during a follow up surgical procedure. The control unit may be placed adjacent to wireless receiver 120, or may be implanted in direct electrical contact with connector 64 (FIG. 15).

Figure 16:
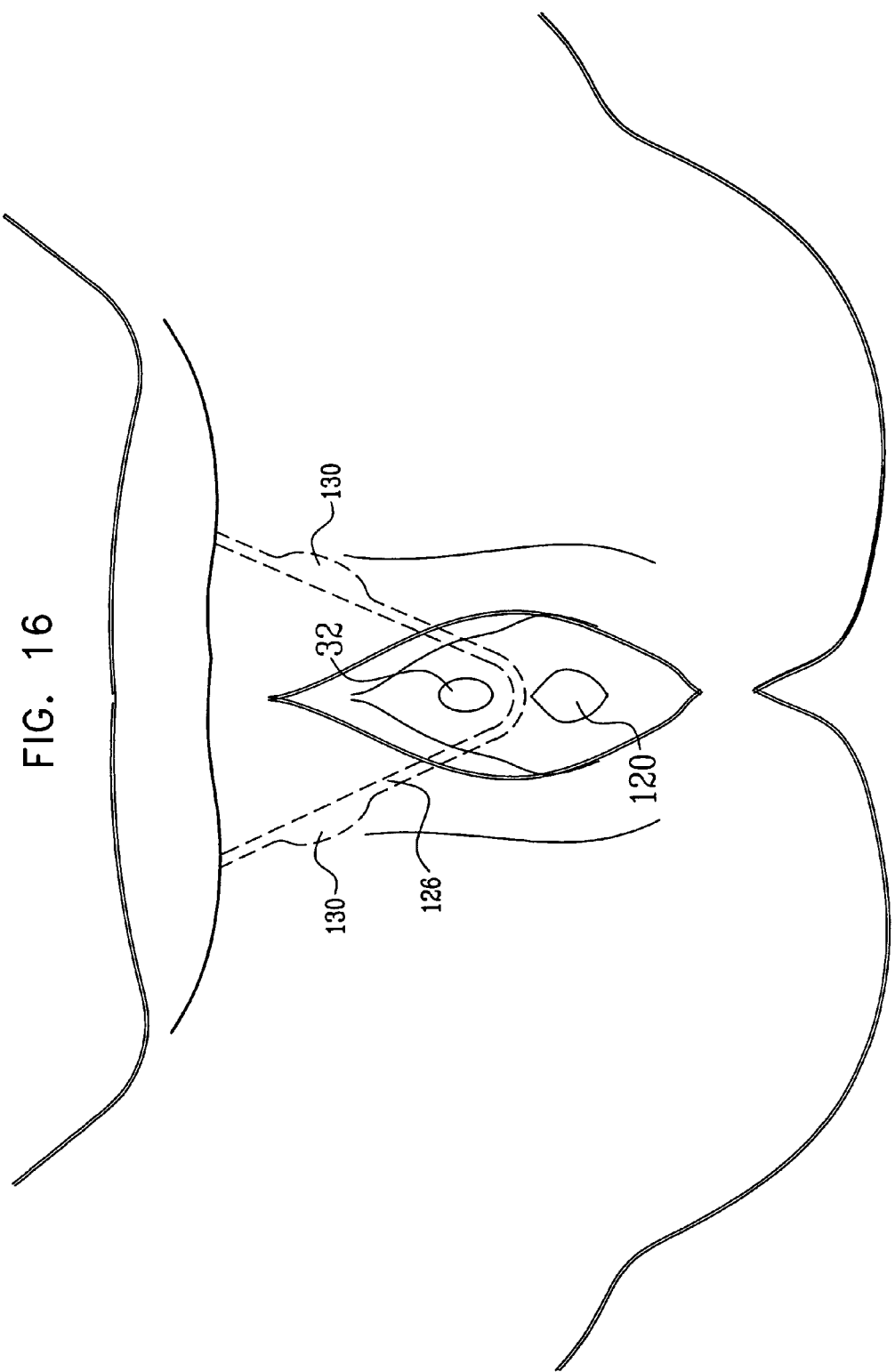
FIGS. 16 and 17 are schematic illustrations of pelvic treatment apparatus implanted in a female patient, in two respective phases of the apparatus, in accordance with an embodiment of the present invention.

FIG. 16 is a schematic illustration of pelvic treatment apparatus comprising a mechanical support 126, in accordance with an embodiment of the present invention. Mechanical support 126 is shaped to define one or more pockets 130 that are typically filled with a viscous substance that can flow within the mechanical support in response to force applied by pelvic musculature, in particular at force levels associated with the onset of stress incontinence. FIG. 16 shows mechanical support 126 when no stress-incontinence-related force is being applied by the pelvic musculature on the support. In this disposition, the mechanical support is typically providing only minimal support, if any, to urethra 32. Alternatively, the mechanical support generally continuously provides support to the urethra.

Figure 17:
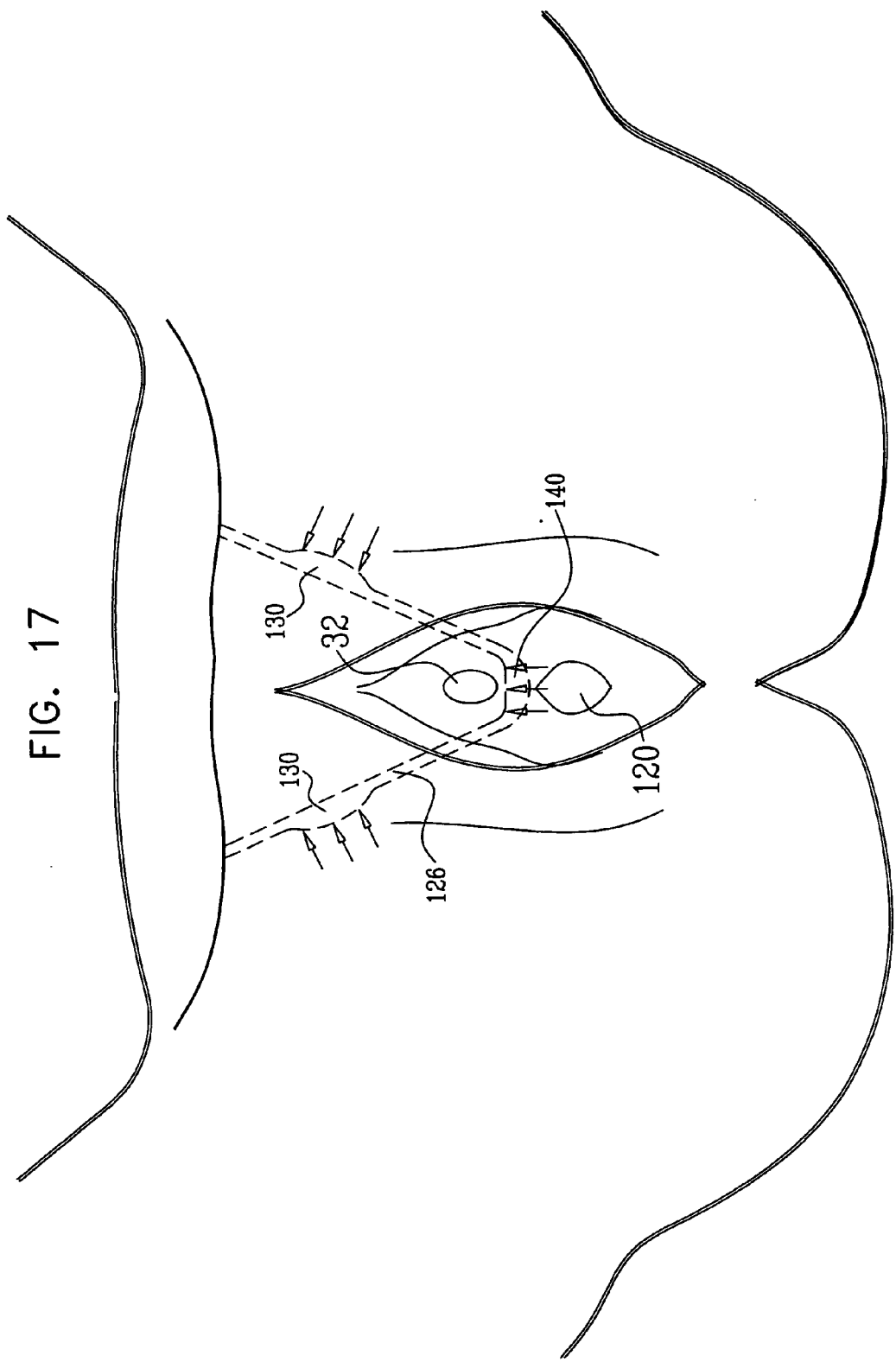

FIG. 17 is a schematic illustration of the apparatus of FIG. 16, during the application of force normally associated with the onset of stress incontinence, in accordance with an embodiment of the present invention. In this figure, a portion of the viscous substance within pockets 130 is forced to flow towards a region 140 of mechanical support 126 between urethra 32 and vagina 120 of the patient. The extra volume within region 140 transiently supports the urethra and prevents or minimizes involuntary voiding. Subsequently, elasticity of region 140 ejects the excess viscous substance from the region, and this returns to pockets 130. Alternatively or additionally, the pockets have an unstressed disposition in which their volume is substantially larger than when they are squeezed by the pelvic musculature, and they therefore draw back the viscous substance.

Figure 18:
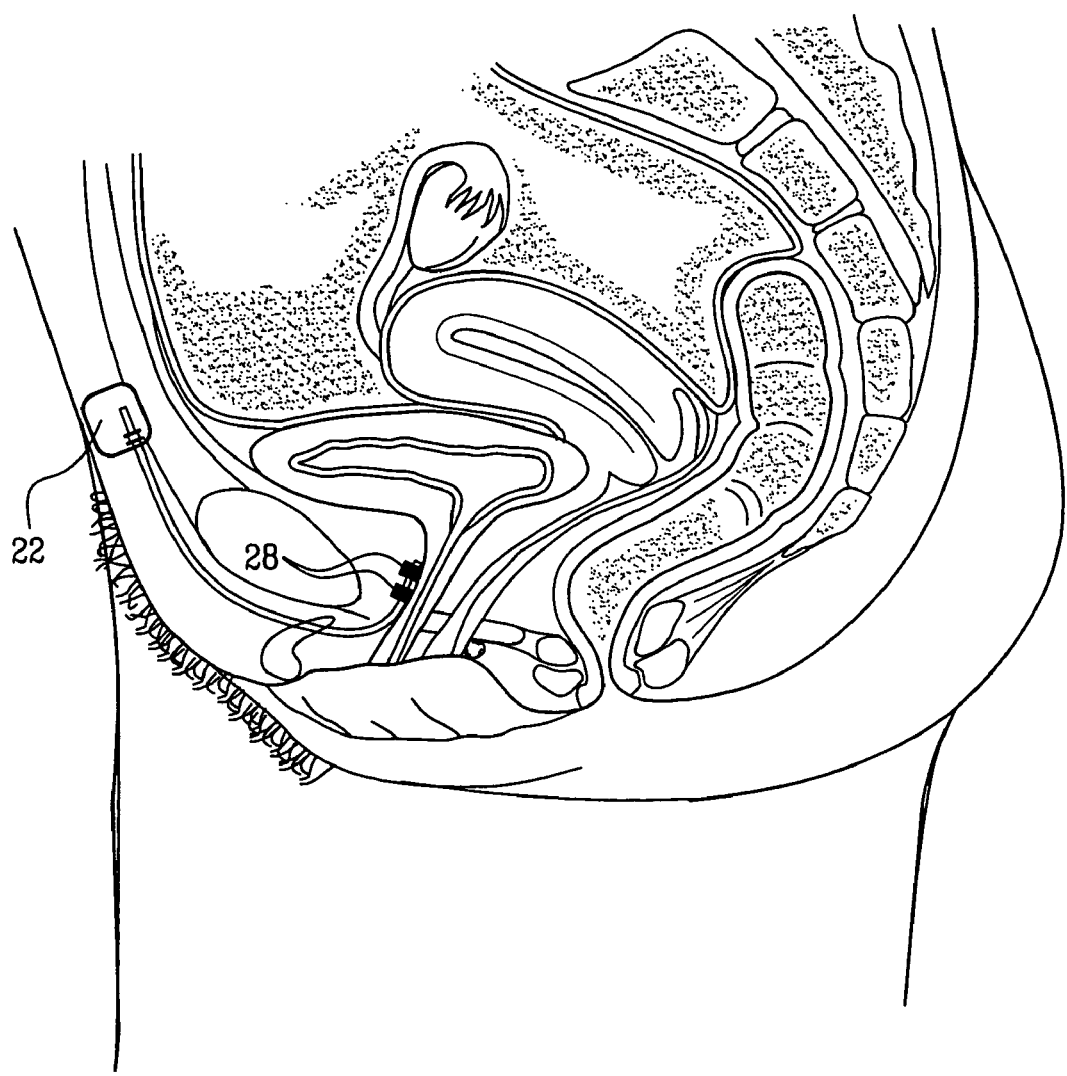
FIGS. 18 and 19 are schematic illustrations of pelvic treatment apparatus implanted in a female patient, in two respective phases of the apparatus, in accordance with another embodiment of the present invention.
Figure 19:
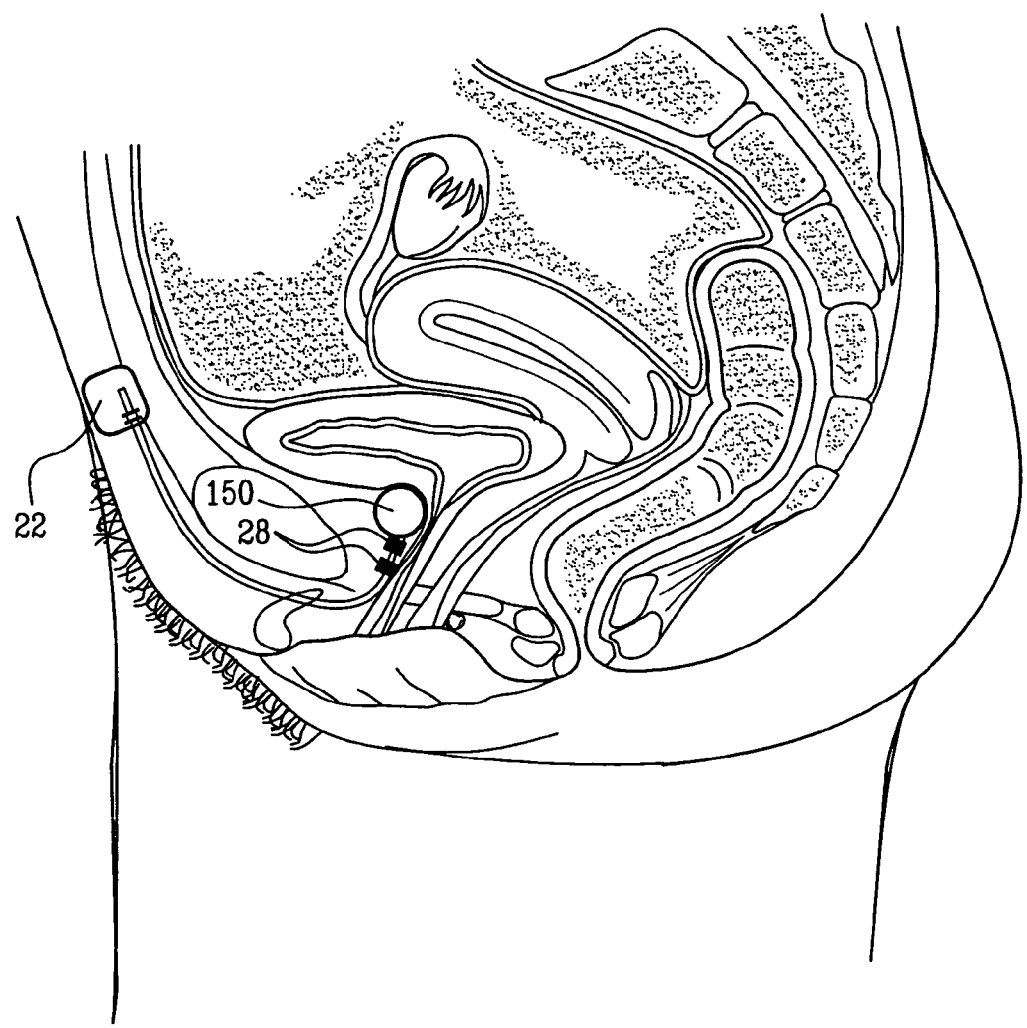

Reference is now made to FIGS. 18 and 19, which are schematic illustrations of pelvic treatment apparatus, in two respective phases thereof, in accordance with an embodiment of the present invention. FIG. 18 shows an implantation procedure in which control unit 22 and electrodes 28 are placed within the body of a female patient. In FIG. 19, a mechanical support comprising a balloon 150 coupled to the electrodes is inflated, in order to provide support of pelvic musculature and thereby treat stress incontinence. At intermittent times following implantation of the mechanical support, the pressure in the balloon is evaluated and regulated, as appropriate.

It is to be understood that embodiments of the present invention are described hereinabove with respect to using a mechanical support to treat stress incontinence by way of illustration and not limitation. The scope of the present invention includes using a mechanical support to treat other pelvic conditions (e.g., cystocele and pelvic organ prolapse), as well. Similarly, various embodiments of the invention are described herein with respect to applying electrical current to treat urge incontinence by way of illustration and not limitation. The scope of the present invention includes using the same techniques of applying current to treat other conditions (e.g., bladder dysfunction, mixed incontinence, overactive bladder, interstitial cystitis, and fecal incontinence), as well.

For these conditions, techniques described in U.S. Pat. No. 6,862,480 to Cohen et al. are typically utilized.

Embodiments of the present invention are generally suitable for use with male and female patients.

Techniques described in the present patent application may be practiced in combination with techniques described in one or more of the patent references cited in the Background section of the present patent application. By way of illustration and not limitation, techniques described herein may be practiced in combination with techniques described in U.S. Pat. Nos. 6,652,450, 6,612,977, 6,802,807, 6,712,772, and 6,911,003. Each of these patents is incorporated herein by reference.

US Patent Application Publication 2003/0171644 describes an implantable device with helical and spiral needles that are used for implanting mesh and or tape into a patient. US Patent Application Publication 2005/0143618 describes an approach for treating male stress urinary incontinence using helical and spiral needles, via a transobturator approach. Each of these applications is incorporated herein by reference. Techniques described herein may be practiced in combination with suprapubic, transvaginal, retropubic or transobturator approach techniques described therein, as well as other techniques described therein.

Mechanical supports as described herein may be implemented using techniques described in U.S. Pat. No. Application Publications 2005/0245787 and 2005/0250977, which are incorporated herein by reference, or using techniques described in other references cited in the Background section of the present patent application or as are known in the art. Mechanical support 26 may comprise any suitable material known in the art, such as a synthetic material, a polymer, cadaveric material, an autologous material, or a biological material such as porcine dermis.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method, comprising:
providing an implantable member comprising mesh and at least one electrode;
making at least one incision in a patient;
implanting the member in contact with pelvic tissue of the patient comprising passing the implantable member through the at least one incision;
driving a current through the at least one electrode into the pelvic tissue of the patient; and
implanting a control unit in the patient comprising passing the control unit through the at least one incision, wherein driving a current through the at least one electrode comprises driving a current through the at least one electrode using the control unit.

2. The method according to claim 1, wherein the mesh forms a sling.

3. The method according to claim 1, comprising inducing relaxation of a pelvic muscle of the patient responsive to driving a current.

4. The method according to claim 1, comprising treating a condition of the patient responsive to driving a current through the at least one electrode, wherein the condition of the patient is selected from the group consisting of: urge incontinence, bladder dysfunction, mixed incontinence, overactive bladder, interstitial cystitis, and fecal incontinence.

5. The method according to claim 1, comprising treating incontinence of the patient responsive to driving a current through the at least one electrode.

6. The method of claim 5, wherein treating incontinence of the patient responsive to driving a current through the at least one electrode comprises contracting the urinary sphincter of the patient.

7. The method according to claim 1, comprising inducing relaxation of a bladder muscle of the patient without contracting a pelvic muscle of the patient responsive to driving a current through the at least one electrode.

8. The method according to claim 1, comprising treating incontinence responsive to driving a current.

9. The method according to claim 8, comprising generating a signal indicative of imminent incontinence of the patient.

10. The method of claim 1, further comprising treating urge incontinence of the patient responsive to driving a current.

11. The method of claim 1, wherein the at least one electrode is coupled to the mesh.

12. The method of claim 1, further comprising mechanically supporting a pelvic structure of the patient using the mesh.

13. The method according to claim 12, comprising treating incontinence responsive to mechanically supporting a pelvic structure of the patient using the mesh.

14. The method according to claim 12, comprising treating cystocele responsive to mechanically supporting a pelvic structure of the patient using the mesh.

15. The method according to claim 12, comprising treating pelvic organ prolapse responsive to mechanically supporting a pelvic structure of the patient using the mesh.

16. The method according to claim 12, wherein mechanically supporting a pelvic structure of the patient comprises accessing the pelvic structure via an approach selected from the group consisting of: a suprapubic approach, a transvaginal approach, a retropubic approach, and a transobturator approach.

17. The method of claim 12, wherein mechanically supporting comprises anchoring the member to structure of the patient other than the pelvic structure.

18. The method according to claim 12, wherein:
mechanically supporting a pelvic structure of the patient comprises mechanically supporting a portion of the urethra of the patient with the mesh;
the at least one electrode comprises a plurality of electrodes; and
driving a current comprises driving the current from the plurality of electrodes which are aligned around less than 180 degrees of the urethra.

19. The method according to claim 18, comprising:
at a pre-implantation time prior to a first time of mechanically supporting the portion of the urethra, identifying the patient as not suffering from urge incontinence; and
at a post-implantation time subsequent to the first time of mechanically supporting the portion of the urethra, identifying the patient as suffering from urge incontinence, wherein driving the current comprises:
not driving the current on each of any 30 consecutive days prior to the post-implantation time; and
driving the current on each of at least 30 consecutive days following the post-implantation time.

20. The method according to claim 18, wherein driving a current comprises starting to drive a current on each of at least 30 consecutive days at a time greater than 60 days from a first time of mechanically supporting the portion of the urethra.

21. The method according to claim 20, comprising treating at least one condition responsive to driving a current, wherein the at least one condition including a condition that is not stress incontinence.

22. A method, comprising:
providing an implantable member comprising mesh and a plurality of electrodes;
making at least one incision in a patient;
implanting the member in contact with pelvic tissue of the patient comprising passing the implantable member through the at least one incision;
mechanically supporting a pelvic structure of the patient using the mesh comprising mechanically supporting a portion of the urethra of the patient with the mesh, wherein the electrodes are aligned around less than 180 degrees of the urethra; and
driving a current through at least one of the plurality of electrodes into the pelvic tissue of the patient, comprising starting to drive a current on each of at least 30 consecutive days at a time greater than 60 days from a first time of mechanically supporting the portion of the urethra.

23. The method according to claim 22, comprising treating at least one condition responsive to driving a current, wherein the at least one condition including a condition that is not stress incontinence.

24. The method according to claim 22, comprising treating incontinence responsive to mechanically supporting a pelvic structure of the patient using the mesh.

25. The method according to claim 22, comprising treating cystocele responsive to mechanically supporting a pelvic structure of the patient using the mesh.

26. The method according to claim 22, comprising treating pelvic organ prolapse responsive to mechanically supporting a pelvic structure of the patient using the mesh.

27. The method according to claim 22, wherein the mesh forms a sling.

28. The method according to claim 22, wherein mechanically supporting a pelvic structure of the patient comprises accessing the pelvic structure via an approach selected from the group consisting of: a suprapubic approach, a transvaginal approach, a retropubic approach, and a transobturator approach.

29. The method according to claim 22, comprising inducing relaxation of a pelvic muscle of the patient responsive to driving a current.

30. The method according to claim 22, comprising treating a condition of the patient responsive to driving a current, wherein the condition of the patient is selected from the group consisting of: urge incontinence, bladder dysfunction, mixed incontinence, overactive bladder, interstitial cystitis, and fecal incontinence.

31. The method according to claim 22, comprising treating incontinence of the patient responsive to driving a current through the at least one electrode.

32. The method according to claim 22, comprising inducing relaxation of a bladder muscle of the patient without contracting a pelvic muscle of the patient responsive to driving a current.

33. The method according to claim 22, comprising implanting a control unit in the patient comprising passing the control unit through the at least one incision, wherein driving a current through at least one of the plurality of electrode comprises driving a current through at least one of the plurality of electrodes using the control unit.

34. A method, comprising:
providing an implantable member comprising mesh and a plurality of electrodes;
making at least one incision in a patient;
implanting the member in contact with pelvic tissue of the patient comprising passing the implantable member through the at least one incision;
mechanically supporting a pelvic structure of the patient using the mesh comprising mechanically supporting a portion of the urethra of the patient with the mesh, wherein the electrodes are aligned around less than 180 degrees of the urethra; and
driving a current through at least one of the plurality of electrodes into the pelvic tissue of the patient;
wherein:
at a pre-implantation time prior to a first time of mechanically supporting the portion of the urethra, identifying the patient as not suffering from urge incontinence; and
at a post-implantation time subsequent to the first time of mechanically supporting the portion of the urethra, identifying the patient as suffering from urge incontinence, wherein driving the current comprises:
not driving the current on each of any 30 consecutive days prior to the post-implantation time; and
driving the current on each of at least 30 consecutive days following the post-implantation time.

35. The method according to claim 34, comprising treating at least one condition responsive to driving a current, wherein the at least one condition including a condition that is not stress incontinence.

36. The method according to claim 34, comprising treating incontinence responsive to mechanically supporting a pelvic structure of the patient using the mesh.

37. The method according to claim 34, comprising treating cystocele responsive to mechanically supporting a pelvic structure of the patient using the mesh.

38. The method according to claim 34, comprising treating pelvic organ prolapse responsive to mechanically supporting a pelvic structure of the patient using the mesh.

39. The method according to claim 34, wherein the mesh forms a sling.

40. The method according to claim 34, wherein mechanically supporting a pelvic structure of the patient comprises accessing the pelvic structure via an approach selected from the group consisting of: a suprapubic approach, a transvaginal approach, a retropubic approach, and a transobturator approach.

41. The method according to claim 34, comprising inducing relaxation of a pelvic muscle of the patient responsive to driving a current.

42. The method according to claim 34, comprising treating a condition of the patient responsive to driving a current, wherein the condition of the patient is selected from the group consisting of: urge incontinence, bladder dysfunction, mixed incontinence, overactive bladder, interstitial cystitis, and fecal incontinence.

43. The method according to claim 34, comprising treating incontinence of the patient responsive to driving a current through the at least one electrode.

44. The method according to claim 34, comprising inducing relaxation of a bladder muscle of the patient without contracting a pelvic muscle of the patient responsive to driving a current.

45. The method according to claim 34, comprising implanting a control unit in the patient comprising passing the control unit through the at least one incision, wherein driving a current through at least one of the plurality of electrode comprises driving a current through at least one of the plurality of electrodes using the control unit.

\* \* \* \* \*